United States Patent
Thomson et al.

(10) Patent No.: US 11,739,369 B2
(45) Date of Patent: Aug. 29, 2023

(54) IMMUNE PROFILING USING SMALL VOLUME BLOOD SAMPLES

(71) Applicant: California Institute of Technology, Pasadena, CA (US)

(72) Inventors: Matthew W. Thomson, Pasadena, CA (US); Tatyana Dobreva, Pasadena, CA (US); David Brown, Pasadena, CA (US); Jong Hwee Park, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 27 days.

(21) Appl. No.: 17/209,229

(22) Filed: Mar. 23, 2021

(65) Prior Publication Data
US 2021/0324447 A1    Oct. 21, 2021

Related U.S. Application Data

(60) Provisional application No. 62/993,541, filed on Mar. 23, 2020.

(51) Int. Cl.
*C12P 19/34* (2006.01)
*C12Q 1/6806* (2018.01)
*C12Q 1/6869* (2018.01)

(52) U.S. Cl.
CPC ......... *C12Q 1/6806* (2013.01); *C12Q 1/6869* (2013.01); *C12Q 2600/112* (2013.01)

(58) Field of Classification Search
CPC .................................................. C12Q 1/6869
See application file for complete search history.

(56) References Cited

U.S. PATENT DOCUMENTS

| | | |
|---|---|---|
| 2010/0221712 A1 | 9/2010 | Radford et al. |
| 2020/0090782 A1 | 3/2020 | Thomson et al. |
| 2022/0033774 A1* | 2/2022 | Oh ....................... C12N 5/0093 |

OTHER PUBLICATIONS

Blicharz et al., "Microneedle-based device for the one-step painless collection of capillary blood samples," Nature Biomedical Engineering 2018, 2, 151-157.
Braun et al., "Universal method for robust detection of circadian state from gene expression," PNAS 2018, 115(39), E9247-E9256.
Brodin & Davis, "Human immune system variation," Nat Rev Immunol 2017, 17(1), 21-29.
Cai et al., "Single-cell transcriptomics of blood reveals a natural killer cell subset depletion in tuberculosis," EBioMedicine 2020, 53(102686), 1-11.
Catala et al., "Quantitative metabolomics comparison of traditional blood draws and TAP capillary blood collection," Metabolics 2018, 14(100), abstract only.
Chang et al., "Circadian control of the secretory pathway maintains collagen homeostasis," Nature Cell Biology 2020, 22(1), 74-86.
Chen et al., "Genetic Drivers of Epigenetic and Transcriptional Variation in Human Immune Cells," Cell 2016, 167, 1398-1414.
Chen et al., "PBMC fixation and processing for Chromium single-cell RNA sequencing," J Transl Med 2018, 16(198), in 11 pages.
De Jager et al., "ImmVar project: Insights and design considerations for future studies of "healthy" immune variation," Semin Immunol 2015, 27(1), 51-57.
Der et al., "Tubular Cell and Keratinocyte Single-cell Transcriptomics Applied to Lupus Nephritis Reveal Type I IFN and Fibrosis Relevant Pathways," Nat Immunol 2019, 20(7), 915-927.
Dimitrov et al., "Cortisol and epinephrine control opposing circadian rhythms in T cell subsets," Blood 2009, 113, 5134-5143.
Dobreva et al., "Single cell profiling of capillary blood enables out of clinic human immunity studies," Scientific Reports 2020, 10(20540), 1-9.
Dobreva et al., "Enabling out-of-clinic human immunity studies via single-cell profiling of capillary blood," bioRxiv 2020, 210468, in 15 pages, doi: https://doi.org/10.1101/2020.07.25.210468.
Fairfax & Knight, "Genetics of gene expression in immunity to infection," Curr Opin Immunol 2014, 30, 63-71.
Farh et al., "Genetic and epigenetic fine mapping of causal autoimmune disease variants," Nature 2015, 518, 337-343.
Foo et al., "Longitudinal transcriptome-wide gene expression analysis of sleep deprivation treatment shows involvement of circadian genes and immune pathways," Translational Psychiatry 2019, 9(343), in 10 pages.
Gate et al., "Clonally expanded CD8 T cells patrol the cerebrospinal fluid in Alzheimer's disease," Nature 2020, 577, 399-404.
Hashimoto et al., "Single-cell transcriptomics reveals expansion of cytotoxic CD4 T-cells in 1 supercentenarians," bioRxiv 2019, 643528, in 52 pages, doi: https://doi.org/10.1101/643528.
He et al., "Circadian Expression of Migratory Factors Establishes Lineage-Specific Signatures that Guide the Homing of Leukocyte Subsets to Tissues," Immunity 2018, 49, 1175-1190.
Hermida et al., "Administration-time-dependent effects of Olmesartan on the ambulatory blood pressure of essential hypertension patients," Chronobiol Int 2009, 26(1), 61-79.
Hu et al., "Single-cell Transcriptome Mapping Identifies Common and Cell-type Specific Genes Affected by Acute Delta9-tetrahydrocannabinol in Humans," Scientific Reports 2020, 10(3450), 1-14.
International Search Report and Written Opinion dated Jul. 6, 2021 in PCT Application No. PCT/US2021/023547.
Kanehisa & Goto, "KEGG: Kyoto Encyclopedia of Genes and Genomes," Nucleic Acids Res. 2000, 28(1), 27-30.
Kanehisa, "Toward understanding the origin and evolution of cellular organisms," Protein Science 2019, 28, 1947-1951.

(Continued)

*Primary Examiner* — Kenneth R Horlick
(74) *Attorney, Agent, or Firm* — Sheppard, Mullin, Richter & Hampton LLP

(57) ABSTRACT

The present disclosure provides methods, systems, devices, kits, and reagents for performing single cell sequencing (e.g., single cell RNA sequencing) from a low volume, capillary blood (or any low volume blood sample which is not obtained from a vein or by venipuncture).

20 Claims, 11 Drawing Sheets

(56) References Cited

OTHER PUBLICATIONS

Kanehisa et al., "New approach for understanding genome variations in KEGG," Nucleic Acids Research, 2019, 47, D590-D595.

Kang et al., "Multiplexed droplet single-cell RNA-sequencing using natural genetic variation," Nat Biotechnol 2018, 36(1), 89-94.

Kazer et al., "Integrated single-cell analysis of multicellular immune dynamics during hyperacute HIV-1 infection," Nature Medicine 2020, 26, 511-518.

Keller et al., "A circadian clock in macrophages controls inflammatory immune responses," PNAS 2009, 106(50), 21407-21412.

Kobayashi et al., "Circadian chemotherapy for gynecological and genitourinar cancers," Chronobiology International 2002, 19(1), 237-251.

Krleza et al., "Capillary blood sampling: national recommendations on behalf of the Croatian Society of Medical Biochemistry and Laboratory Medicine," Biochemia Medica 2015, 25(3), 335-358.

Kusanagi et al., "Expression profiles of 10 circadian clock genes in human peripheral blood mononuclear cells," Neuroscience Research 2008, 61(2), 136-142.

Lappalainen et al., "Transcriptome and genome sequencing uncovers functional variation in humans," Nature 2013, 501 (7468), 506-511.

Lech et al., "Dissecting Daily and Circadian Expression Rhythms of Clock-Controlled Genes in Human Blood," Journal of Biological Rhythms 2016, 31(1), 68-81.

Lee et al., "Immunophenotyping of COVID-19 and influenza highlights the role of type I interferons in development of severe COVID-19," Science Immunology 2020, in 16 pages.

Lévi et al., "Implications of circadian clocks for the rhythmic delivery of cancer therapeutics," Philos Trans A Math Phys Eng Sci 2008, 366(1880), 3575-3598.

Long et al., "Morning vaccination enhances antibody response over afternoon vaccination: A cluster-randomised trial," Vaccine 2016, 34(24), 2679-2685.

Lopez et al., "Deep Generative Modeling for Single-cell Transcriptomics," Nat Methods 2018, 15(12), 1053-1058.

Martin et al., "Single-Cell Analysis of Crohn's Disease Lesions Identifies a Pathogenic Cellular Module Associated with Resistance to Anti-TNF Therapy," Cell 2019, 178(6), 1493-1508.

Matsa et al., "Transcriptome profiling of patient-specific human iPSC-cardiomyocytes predicts individual drug safety and efficacy responses in vitro," Cell Stem Cell 2016, 19(3), 311-325.

Orange et al., "RNA Identification of PRIME Cells Predicting Rheumatoid Arthritis Flares," The New England Journal of Medicine 2020, 383(3), 218-228.

Pick et al., "Time-of-Day-Dependent Trafficking and Function of Leukocyte Subsets," Trends in Immunology 2019, 40(6), 524-537.

Pulford et al., "Lymphocyte-specific protein 1: a specific marker of human leucocytes," Immunology 1999, 96, 262-271.

Ramsey & Ellisen, "Circadian function in cancer: Regulating the DNA damage response," PNAS 2011, 108(26), 10379-10380.

Ren et al., "COVID-19 immune features revealed by a large-scale single-cell transcriptome atlas," Cell 2021, 184, 1-19.

Robison et al., "Whole genome transcript profiling from fingerstick blood samples: a comparison and feasibility study," BMC Genomics 2009, 10(617), in 9 pages.

Seumois et al., "Single-cell transcriptomic analysis of allergen-specific T cells in allergy and asthma," Science Immunology 2020, 5, 1-15.

Sumitomo et al., "Transcriptome analysis of peripheral blood from patients with rheumatoid arthritis: a systematic review," Inflammation and Regeneration 2018, 38(21), in 5 pages.

Tang et al., "Capillary blood for point-of-care testing," Critical Reviews in Clinical Laboratory Sciences 2017, 54(5), 294-308.

Thomas, "Gene-Environment-Wide Association Studies: Emerging Approaches," Nat Rev Genet 2010, 11(4), 259-272.

Toma et al., "A clinically validated human capillary blood transcriptome test for global systems biology studies," BioTechniques 2020, 69(4), 289-301.

Tsang et al., "Global Analyses of Human Immune Variation Reveal Baseline Predictors of Postvaccination Responses," Cell 2014, 157, 499-513.

Uhlén et al., "Tissue-based map of the human proteome," Science 2015, 347(6220), in 12 pages.

Uniken Venema et al., "Single-Cell RNA Sequencing of Blood and Ileal T Cells From Patients With Crohn's Disease Reveals Tissue-Specific Characteristics and Drug Targets," Gastroenterology 2019, 156(3), 812-815.

Van Der Wijst et al., "Single-cell RNA sequencing identifies cell type-specific cis-eQTLs and co-expression QTLs," Nat Genet. 2018, 50(4), 493-497.

Whitney et al., "Individuality and variation in gene expression patterns in human blood," PNAS 2003, 100(4), 1896-1901.

Wittenbrink et al., "High-accuracy determination of internal circadian time from a single blood sample," J Clin Invest 2018, 128(9), 3826-3839.

Wu et al., "Peripheral T cell expansion predicts tumour infiltration and clinical response," Nature 2020, 579, 274-278.

Xu et al., "Genotype-free demultiplexing of pooled single-cell RNA-seq," Genome Biology 2019, 20(290), in 12 pages.

Ye et al., "Intersection of population variation and autoimmunity genetics in human T cell activation," Science 2014, 345(6202), in 21 pages.

Zhao et al., "Uncovering the mystery of opposite circadian rhythms between mouse and human leukocytes in humanized mice," Blood 2017, 130(18), 1995-2005.

\* cited by examiner

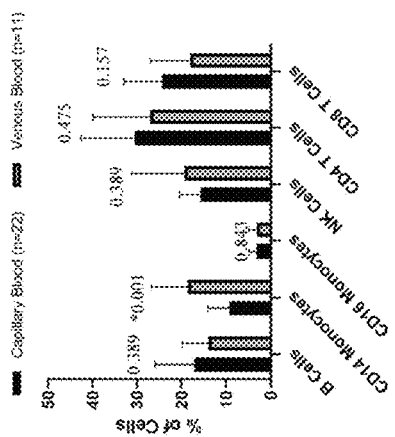
FIG. 1A
FIG. 1B
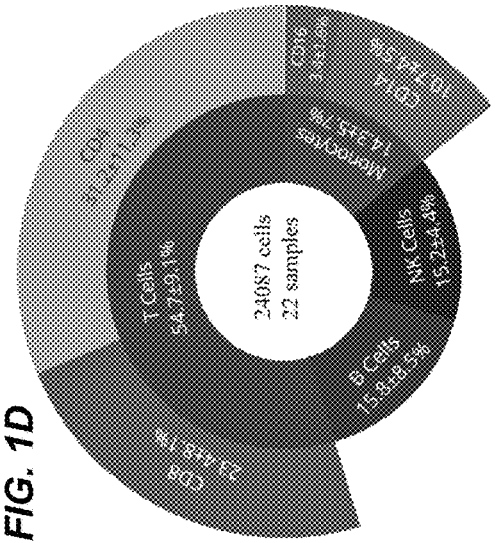
FIG. 1C
FIG. 1D
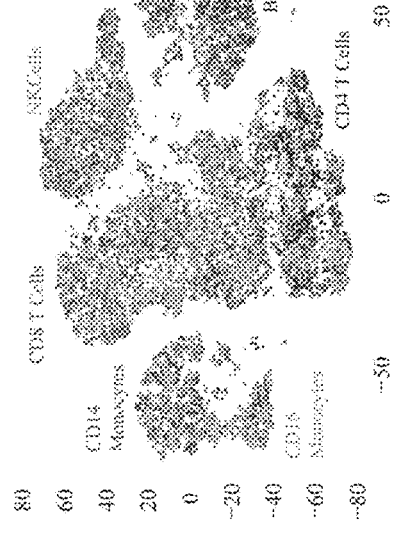
FIG. 1E

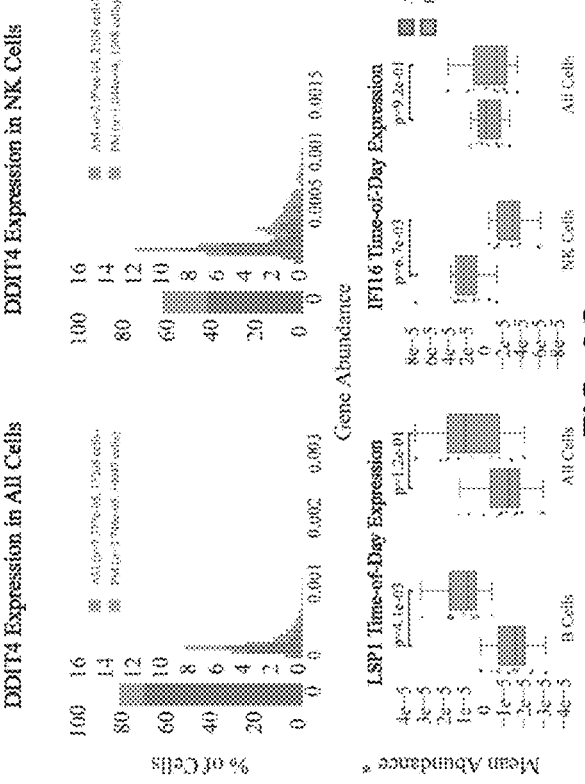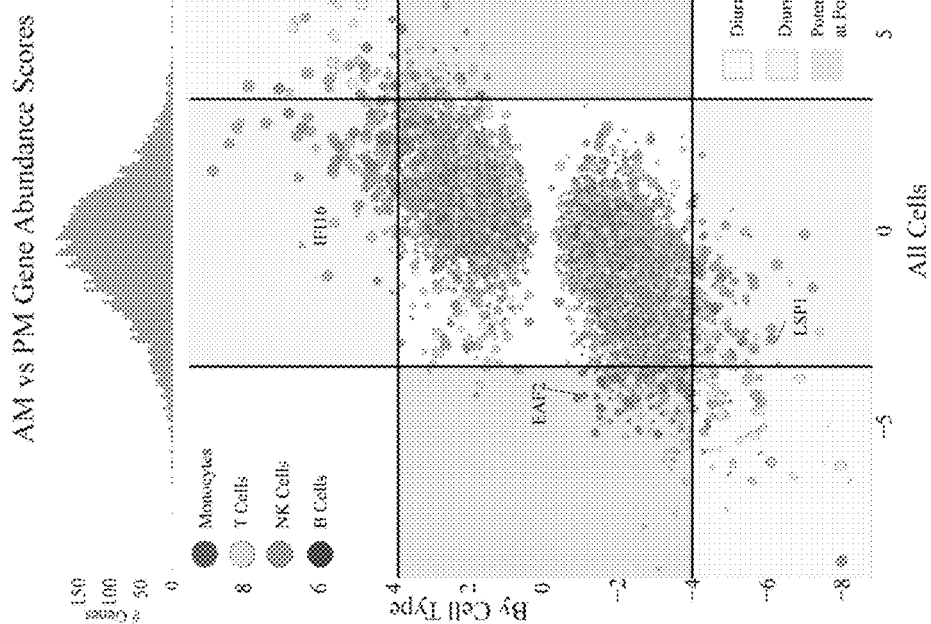
FIG. 2A  FIG. 2B  FIG. 2C  FIG. 2D

IMMUNE PROFILING USING SMALL VOLUME BLOOD SAMPLES

CROSS-REFERENCE TO RELATED APPLICATIONS

This application claims the benefit of priority to U.S. Provisional Patent Application No. 62/993,541, filed on Mar. 23, 2020, and the content of which is incorporated herein by reference in its entirety.

BACKGROUND

Field

This disclosure relates generally to the field of molecular biology, and more particularly to the use of small volume of blood samples for immune profiling.

Background

Increasing evidence implicates the immune system in an overwhelming number of diseases, and distinct cell types play specific roles in their pathogenesis. Studies of peripheral blood have uncovered a wealth of associations between gene expression, environmental factors, disease risk, and therapeutic efficacy. For example, in rheumatoid arthritis, multiple mechanistic paths have been found that lead to disease, and gene expression of specific immune cell types can be used as a predictor of therapeutic non-response. Furthermore, vaccines, drugs, and chemotherapy have been shown to yield different efficacy based on time of administration, and such findings have been linked to the time-dependence of gene expression in downstream pathways. However, human immune studies of gene expression between individuals and across time remain limited to a few cell types or time points per subject, constraining our understanding of how networks of heterogeneous cells making up each individual's immune system respond to adverse events and change over time. There is a need for cost effective, easy-to-access, and non-invasive methods for immune profiling.

SUMMARY

Disclosed herein include embodiments of a method for single cell ribonucleic acid sequencing. In some embodiments, the method comprises providing a first low volume, capillary blood sample (or any low volume blood sample and/or any blood sample not obtained from a vein or by venipuncture) obtained from a subject at a first time point. The method can comprise diluting the first sample to obtain a first diluted sample. The method can comprise isolating first capillary peripheral blood mononuclear cells (cPBMCs) from the first diluted sample with gradient centrifugation. The method can comprise performing single cell ribonucleic acid sequencing (scRNA-seq) on the first cPBMCs isolated to generate first scRNA-seq data. The method can comprise determining a first scRNA profile of the subject at the first time point using the first scRNA-seq data and single-nucleotide polymorphisms (SNPs) of the subject.

In some embodiments, the method comprises providing a second low volume, capillary blood sample obtained from a subject at a second time point. The method can comprise diluting the second sample to obtain a second diluted sample. The method can comprise isolating second cPBMCs from the second diluted sample with gradient centrifugation. The method can comprise performing scRNA-seq on the second cPBMCs isolated to generate second scRNA-seq data. The method can comprise determining a second scRNA profile of the subject at the second time point using the second scRNA-seq data and SNPs of the subject.

In some embodiments, the first time point and the second time point are about 2 hours to about 24 hours apart. In some embodiments, the subject is in a first health state at the first time point, and the subject is in a second health state at the second time point. The first health state at the first time point can comprise a first disease state of a disease, and the second health state at the second time point can comprise a second disease state of the disease. The first health state at the first time point can comprise first symptoms, and the second health state at the second time point can comprise second symptoms. The first symptoms and the second symptoms can be identical, the first symptoms and the second symptoms can be different, the first symptoms can comprise the second symptoms, and/or the second symptoms can comprise the first symptoms. The first symptoms and the second symptoms can comprise an identical symptom of different severities. In some embodiments, the method comprises receiving the first health state of the subject at the first time point and the second health state of the subject at the second time point. In some embodiments, the method comprises correlating the first health state of the subject at the first time point with the first scRNA profile of the subject at the first time point. The method can comprise correlating the second health state of the subject at the second time point with the second scRNA profile of the subject at the second time point.

In some embodiments, the method comprises determining a difference between the scRNA profile of the subject at the first time point and the second scRNA profile of the subject at the second time point. The method can thereby determine one or more genes of interest. The one or more genes of interest can comprise diurnal genes. The one or more genes of interest can comprise one or more genes each with a time of day variation in the first scRNA profile and the second scRNA profile. The method can comprise designing a gene panel comprising the one or more genes of interest. The method can comprise determining a difference between the first health state of the subject at the first time point and the second health state of the subject at the second time point. In some embodiments, the method comprises correlating (i) the difference between the scRNA profile of the subject at the first time point and the second scRNA profile of the subject at the second time point and (ii) the difference between the first health state of the subject at the first time point and the second health state of the subject at the second time point.

In some embodiments, said determining comprises: performing sample demultiplexing of the first scRNA data of the subject and/or the second scRNA data of the subject using SNPs of the subject to determine the first scRNA profile of the subject and/or the second scRNA profile of the subject. In some embodiments, performing sample demultiplexing of the first scRNA data of the subject comprises: classifying scRNA-seq reads with an identical cell label in the first scRNA data as reads generated from a cell of a sample obtained from the subject based on (i) SNPs present in one or more of the scRNA-seq reads with the identical cell label and, (ii) optionally, SNPs of the subject. In some embodiments, performing the sample demultiplexing of the first scRNA data of the subject comprises: classifying scRNA-seq reads with an identical cell label in the second scRNA data as reads generated from a cell of a sample obtained from the subject based on SNPs present in one or more of the scRNA-seq reads with the identical cell label and (ii) optionally, SNPs of the subject. The SNPs of the subject can be determined using the first low volume, capillary blood sample of the subject. In some embodiments, the SNPs of the subject are determined by bulk RNA sequencing and/or scRNA sequencing. Said bulk RNA sequencing and/or scRNA sequencing can be performed using a low volume, capillary blood sample of the subject.

Disclosed herein include embodiments of a method for single cell ribonucleic acid sequencing. In some embodiments, the method comprises: providing a plurality of low volume, capillary blood samples (or any low volume blood samples and/or any blood samples not obtained from veins or by venipuncture) obtained from a subject at a plurality of time points. The method can comprise, for each of the plurality of samples, diluting the sample to obtain a diluted sample. The method can comprise isolating capillary peripheral blood mononuclear cells (cPBMCs) from the diluted sample with gradient centrifugation. The method can comprise performing single cell ribonucleic acid sequencing (scRNA-seq) on the cPBMCs isolated to generate scRNA-seq data. The method can comprise determining a scRNA profile of the subject at the time point the sample is collected from the scRNA-seq data and single-nucleotide polymorphisms (SNPs) of the subject. The method can comprise determining one or more differences between scRNA profiles of the subject at two or more of the plurality of time points. In some embodiments, two of the plurality of time points are 2 hours to about 24 hours apart, thereby determining one or more genes of interest. The one or more genes of interest can comprise diurnal genes. The one or more genes of interest can comprise one or more genes each with a time of day variation in the scRNA profiles. The method can comprise designing a gene panel comprising the one or more genes of interest.

In some embodiments, the scRNA-seq comprises a whole transcriptome scRNA-seq. The scRNA profile can comprise a whole transcriptome profile. In some embodiments, the scRNA-seq comprises a target scRNA-seq. The scRNA profile can comprise expression information (e.g., expression profiles) of a plurality of at most 1,000 genes.

Disclosed herein include embodiments of a method for single cell sequencing. In some embodiments, the method comprises providing a plurality of low volume, capillary blood samples (or any low volume blood sample and/or any blood sample not obtained from a vein or by venipuncture) obtained from a plurality of subjects. The method can comprise isolating immune cells from each of the plurality of samples to obtain isolated immune cells. The method can comprise pooling the isolated immune cells of the plurality of subjects to obtain pooled immune cells of the plurality of subjects. The method can comprise performing single cell sequencing on the pooled immune cells of the plurality of subjects to generate single cell sequencing data of the plurality of subjects. The method can comprise determining a single cell profile of each of the plurality of subjects using the single cell sequence data of the plurality of subjects and single-nucleotide polymorphisms (SNPs) of the plurality of subjects.

In some embodiments, the method comprises diluting the plurality of samples to obtain a plurality of diluted sample. Isolating the immune cells from each of the plurality of samples to obtain isolated immune cells can comprise isolating the immune cells from each of the plurality of diluted samples to obtain isolated immune cells.

Disclosed herein include embodiments of a method for single cell sequencing. In some embodiments, the method comprises providing a plurality of low volume, capillary blood samples (or any low volume blood samples and/or any blood samples not obtained from veins or by venipuncture) each obtained from a plurality of subjects. The method can comprise pooling the plurality of samples to obtain a pooled sample. The method can comprise isolating immune cells from the pooled sample to obtain isolated immune cells. The method can comprise performing single cell sequencing on the pooled immune cells to generate single cell sequencing data of the plurality of subjects. The method can comprise determining a single cell profile of each of the plurality of subjects using the single cell sequence data of the plurality of subjects and single-nucleotide polymorphisms (SNPs) of the plurality of subjects.

In some embodiments, the method comprises diluting the pooled sample to obtain a diluted sample, isolating the immune cells from the pooled sample comprises: isolating the immune cells from the diluted sample. In some embodiments, the plurality of samples is collected from the plurality of subjects within one week of each other. In some embodiments, isolating the immune cells comprises isolating the immune cells with gradient centrifugation. In some embodiments, the immune cells comprise peripheral blood mononuclear cells (PBMCs), such as lymphocytes (T cells, B cells, NK cells) and monocytes.

In some embodiments, the single cell sequencing comprises ribonucleic acid (RNA) sequencing, deoxyribonucleic acid (DNA) or DNA-based sequencing (e.g., protein expression profiling), multiomics sequencing, and/or exosome sequencing. The single cell profile can comprise: an RNA expression profile, a protein expression profile, a DNA profile, a multiomics profile, and/or an exome profile.

In some embodiments, said determining comprises: performing sample demultiplexing of the single cell sequencing data of the plurality of subjects using SNPs of the plurality of subjects to determine the single cell profile of each of the plurality of subjects. In some embodiments, performing sample demultiplexing comprises: classifying single cell sequencing reads with an identical cell in the single cell sequencing data as reads generated from a cell of a sample obtained from a subject based on (i) SNPs present in one or more of the single cell sequencing reads and (ii) optionally, SNPs of the one or more subjects of the plurality of subjects. The SNPs of one or each or the one or more subject can be determined by bulk sequencing and/or single cell sequencing. Said bulk sequencing and/or single cell sequencing can be performed using a low volume, capillary blood sample obtained from the subject.

In some embodiments, a single cell profiling of a low volume, capillary blood sample of a first subject of the plurality of subjects has been performed previously, and/or no single cell profiling of any sample or any low volume, capillary blood sample of a second subject of the plurality of subject has been performed previously.

In some embodiments, a sample (e.g., the first sample, the second sample, and/or one, one or more, or each of the plurality of samples) has a volume of about 20 µl to about 500 µl. In some embodiments, a sample is collected by a subject from which the sample is collected from. For example, the first sample is collected by the first subject, the second sample is collected by the second subject, and/or each of the plurality of samples is collected by the subject from whom the sample is obtained from. In some embodiments, a sample (e.g., the first sample, the second sample, and/or each of the plurality of samples) is collected in a non-clinical setting and/or out of clinic. In some embodiments, a sample (e.g., the first sample, the second sample, and/or each of the plurality of samples) is collected using a device comprising microneedles, a device comprising microfluidic channels, a push-button collection device, or a combination thereof. In some embodiments, a sample is collected from a deltoid or a finger of the subject from which the sample is collected. For example, the first sample, the second sample, and/or each of the plurality of samples is collected from a deltoid of the subject at the first time point, a deltoid of the subject at the second time point, and/or a deltoid or a finger of one of the plurality of subjects from which the sample is collected.

In some embodiments, said diluting comprises a 1:2 to 1:50 dilution. In some embodiments, said diluting comprises diluting the first sample, the second sample, and/or each of the plurality of samples having a volume of about 100 µl to about 1 ml. In some embodiments, said diluting comprises diluting using a dilution reagent. In some embodiments, the dilution reagent comprises a buffer and/or a growth medium. In some embodiments, a pH of the buffer is about 7.4. The buffer can comprise sodium chloride, potassium chloride, disodium phosphate, monopotassium phosphate, or a combination thereof. A concentration of sodium chloride can be about 137 mmol/L, a concentration of potassium chloride is about 2.7 mmol/L, a concentration of disodium phosphate is about 10 mmol/L, and/or a concentration of monopotassium phosphate is about 1.8 mmol/L. The buffer can comprise phosphate-buffered saline. In some embodiments, the growth medium comprises fetal bovine serum, bovine serum albumin, a serum-free medium, a protein-free medium, a chemically-defined medium, a peptide-free medium, or a combination thereof. A concentration of the growth medium in the dilution reagent can be about 0.1% to about 10%.

In some embodiments, said isolating comprises isolating the immune cells with gradient centrifugation using a density medium with a density of about 1 g/ml to about 1.5 g/ml. A duration of the density centrifugation can be about 10 mins to about 30 mins. A speed of the density centrifugation can about 500 RPM to about 1500 RPM. In some embodiments, said isolating comprises removing a layer after gradient centrifugation comprising cPBMCs or immune cells, optionally a volume of the layer is about 500 µl to about 1500 µl. Said isolating can comprise removing red blood cells from the layer removed. Removing the red blood cells from the layer removed can comprises lysing the red blood cells.

In some embodiments, the method comprises performing cell typing, diurnal gene detection, subject specific gene detection, cell type specific gene detection, and/or pathway enrichment analysis.

Disclosed herein include embodiments of a system. In some embodiments, the system comprises non-transitory memory configured to store executable instructions; and a processor (e.g., a hardware processor or a virtual processor) in communication with the non-transitory memory, the hardware processor programmed by the executable instructions to perform: receiving a profile comprising a single cell ribonucleic acid (scRNA) profile of each of a plurality of subjects determined using any of any method of the present disclosure. The hardware processor can be programmed by the executable instructions to perform: matching a first scRNA profile of a first subject of the plurality of subjects determined from a first sample obtained at a first time point and a second scRNA profile of a second subject of the plurality of subjects determined from a second sample obtained at a second time point. The first time point can be prior to the second time point. A first profile of the first subject can comprise a first action performed by the first subject and a first associated outcome occurred subsequent to the action being performed. The hardware processor can be programmed by the executable instructions to perform: generating a report or an output (e.g., a file or a visual output) comprising the second scRNA profile, the first action performed by the first subject, the first associated outcome, representations (e.g., visual representations and/or non-visual representations) of one or more of the preceding, or a combination thereof.

Disclosed herein include embodiments of a system. In some embodiments, the system comprises: non-transitory memory configured to store executable instructions and a reference profile comprising a reference single cell profile of each of a plurality of reference subjects determined whether using any method of the disclosure, the reference profile of the reference subject comprises a reference action performed by the reference subject and an associated reference outcome occurred subsequent to the action being performed. The system can comprise a hardware processor in communication with the non-transitory memory, the hardware processor programmed by the executable instructions to perform: receiving a test single cell profile of a test subject determined using any method of the disclosure. The hardware processor can be programmed by the executable instructions to perform: matching the test single cell profile of the test subject to a reference profile of one of the plurality of reference subjects. The hardware processor can be programmed by the executable instructions to perform: generating a report or an output (e.g., a file, or a visual output) comprising the test single cell profile, the reference action performed by the reference subject whose reference single cell profile is matched to the test single cell profile, the associated reference outcome, representations (e.g., visual representations and/or non-visual representations) of one or more of the preceding, or a combination thereof.

Disclosed herein include embodiments of a system. In some embodiments, the system comprises: non-transitory memory configured to store executable instructions and a reference profile comprising a reference single cell profile of each of a plurality of reference subjects determined whether using any method of the disclosure, the reference profile of the reference subject comprises a reference action performed by the reference subject and an associated reference outcome occurred subsequent to the action being performed; and a hardware processor in communication with the non-transitory memory, the hardware processor programmed by the executable instructions to perform: receiving a test single cell profile of a test subject determined using any method of the disclosure. The hardware processor can be programmed by the executable instructions to perform: matching the test single cell profile of the test subject to one or more references profile of one or more of the plurality of reference subjects. The hardware processor can be programmed by the executable instructions to perform: generating a user interface or a report comprising the test single cell profile, the reference action performed by each of the reference subjects whose reference single cell profiles are matched to the test single cell profile, and/or the associated reference outcomes.

In some embodiments, the hardware processor is programmed by the executable instructions to perform: receiving an action of the test subject and an associated test outcome. The hardware processor can be programmed by the executable instructions to perform: storing the action of the test subject and the associated test outcome in the non-transitory memory. In some embodiments, said matching comprises matching using supervised learning, unsupervised learning, or a combination thereof. In some embodiments, the action comprises a non-medical action, a medical action, lack of action, or a combination thereof. In some embodiments, the outcome comprises a positive health outcome. In some embodiments, the outcome comprises a negative health outcome.

Disclosed herein include embodiments of one or more reagents (e.g., a dilution reagent) or devices (e.g., a device for collecting capillary blood) for performing any method of the disclosure. The present disclosure also provides embodiments of a kit comprising one or more reagents for performing any method of the disclosure.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIGS. 1A-E show an exemplary experimental workflow and consistency of capillary blood sampling. FIG. 1A shows an exemplary experimental workflow for capillary blood immune profiling 1. Blood is collected using the TAP device from the deltoid. 2. Capillary peripheral blood mononuclear cells (CPBMCs) are separated via centrifugation. 3. Red blood cells are lysed and removed, and samples from different subjects are pooled together. 4. Cell transcriptomes are sequenced using single-cell sequencing. FIG. 1B shows a time-course study design. CPBMCs are collected and profiled from 4 subjects (2 male, 2 female) each morning (AM) and afternoon (PM) for 3 consecutive days. FIG. 1C shows a 2-dimensional t-SNE projection of the transcriptomes of all cells in all samples. Cells appear to cluster by major cell type (FIG. 9). FIG. 1D shows immune cell type percentages across all samples shows stable cell type abundances (includes cells without subject labels). FIG. 1E shows that cell type ratios between capillary blood from this study, and venous blood from 3 other studies were the same, with the exception of CD14+ Monocytes, which are more abundant in venous blood (FDR<0.05, 2-sided student t-test, multiple comparison corrected). The q-values are displayed for each cell type comparison.

FIGS. 2A-D show diurnal variability in subpopulations of capillary blood. FIG. 2A shows magnitude (Z-score) of the difference in AM vs PM gene expression across the whole population of cells (x) vs the cell type with the largest magnitude Z-score (y). Points above or below the significance lines (FDR<0.05, multiple comparison correction) display different degrees of diurnality. The size of each marker indicates the abundance of the gene (the largest percent of cells in a subpopulation that express this gene). In FIG. 2B, distribution of expression of DDIT4, a previously identified circadian rhythm gene9, shows diurnal signal across all cells, as well as individual cell types, such as natural killer (NK) cells. u indicates the mean fraction of transcripts per cell (gene abundance). FIG. 2C shows example of newly identified diurnal genes, LSP1 and IFI16 that could be missed if analyzed at the population level. FIG. 2D shows that an example of a gene, EAF2, that could be falsely classified as diurnal (i) without considering cell type subpopulations due to a diurnal B cell abundance shift (ii).

In FIG. 3A, magnitude ($\log_2$ F statistic) of the variability in expression of genes between different cell types (x) and between subjects (y). 1284/7034 (18.3%) of genes are above the subject specificity significance line (FDR<0.05, multiple comparison correction) and are classified as subject-specific. Several MEW class II genes (HLA-X) are strongly subject-specific, consistent with previous findings. FIG. 3B shows KEGG pathways grouped into categories and their enrichment (Z-score from 2-proportion Z-test) among the top 250 diurnally and subject-varying genes vs all genes. Immune system and disease pathways are significantly enriched (p=0.029), supportive of the conclusion that immune and disease-related genes are highly subject dependent. The large circles indicate the enrichment of the category overall, and the sizes of the smaller pathway points indicate the number of genes associated with the pathway. FIG. 3C shows subject and cell type specific gene examples for each subject and cell type with the upper row displaying the trace of mean gene expression across time-points and the bottom row showing gene abundance shifts for the subjects of interest.

FIG. 5A is a schematic illustration for the role of S100A8, S100A9, and S100A12 genes in immune regulation. FIG. 5B show normalized mean gene expression of S100A8, S100A9, and S100A12 genes for S2 showing significant downregulation in monocytes as compared to all cells.

In FIG. 8A, agglomerative clustering with n=13 clusters was performed to identify cell types, and annotated using known cell type markers. In FIG. 8B, capillary blood cells cluster together with venous blood cells, with the exception of one cluster of B cells unique to capillary cells, as well as 3 cell types unique to the venous blood sample: red blood cells, dendritic cells, and neutrophils, which are likely filtered out via laboratory procedures and the computational debris filtering pipeline.

Figure 3A:
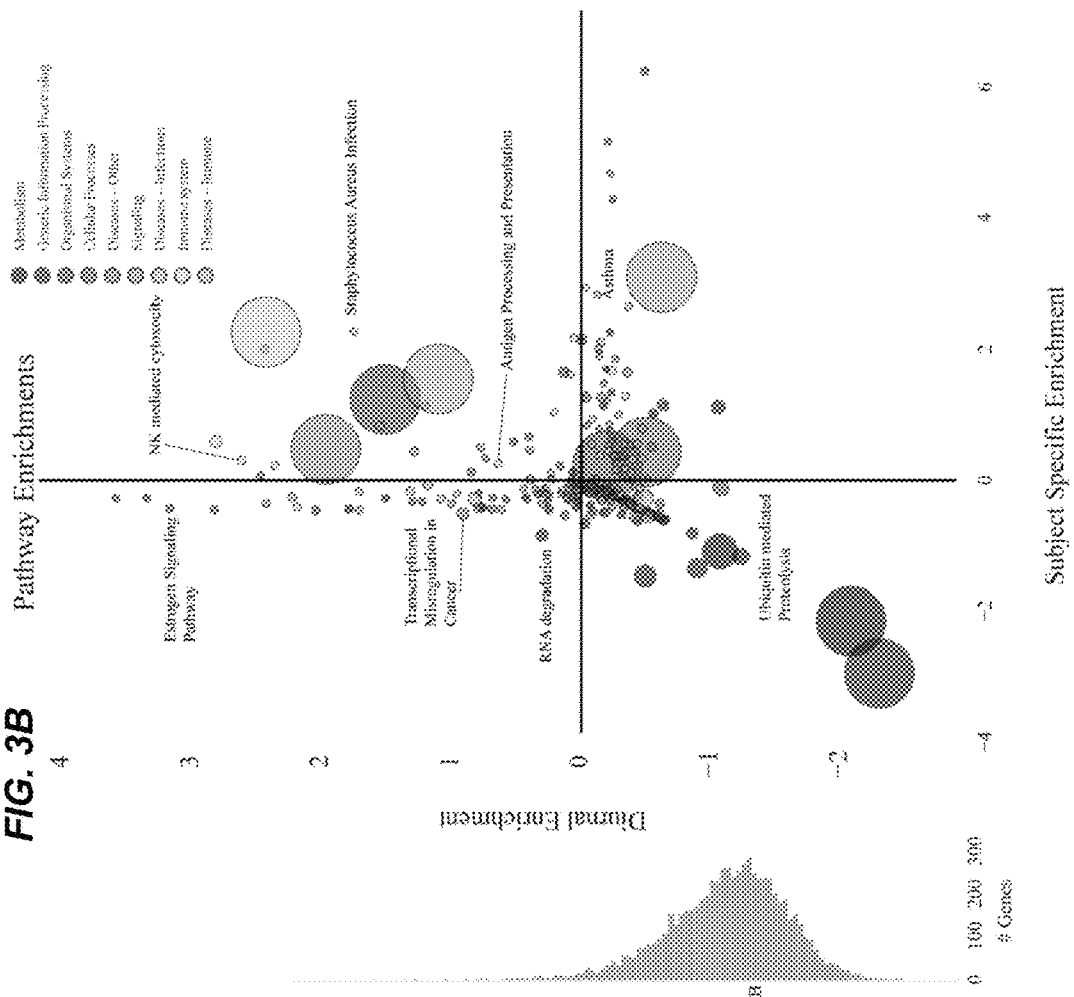
FIGS. 3A-C show subject variability in immune and disease-relevant genes and pathways.

Throughout the drawings, reference numbers may be re-used to indicate correspondence between referenced elements. The drawings are provided to illustrate example embodiments described herein and are not intended to limit the scope of the disclosure.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

An individual's immune system is driven by both genetic and environmental factors that vary over time. As described herein (including Example 1), a platform was developed to leverage multiplexed single-cell sequencing and out-of-clinic capillary blood extraction to enable simplified, cost-effective profiling of the human immune system across people and time at single-cell resolution. The methods, systems and platforms disclosed herein enables better understanding of the temporal and inter-individual variability of gene expression within distinct immune cell types. As shown in Example 1, widespread differences in cell type-specific gene expression were detected between subjects that are stable over multiple days.

The advent of single-cell RNA sequencing (scRNA-seq) has enabled the interrogation of heterogeneous cell populations in blood without cell type isolation and has already been employed in the study of myriad immune-related diseases. Recent studies employing scRNA-seq to study the role of immune cell subpopulations between healthy and ill patients, such as those for Crohn's disease, Tuberculosis, and COVID-19, have identified cell type-specific disease relevant signatures in peripheral blood immune cells; however, these types of studies have been limited to large volume venous blood draws which can tax already ill patients, reduce the scope of studies to populations amenable to blood draws, and often require larger research teams to handle the patient logistics and sample processing costs and labor. In particular, getting repeated venous blood draws within a single day and/or multiple days at the subject's home has been a challenge for older people with frail skin and those on low dosage Acetylsalicylic acid. This dependence on venous blood dramatically limits our ability to understand the high temporal dynamics of health and disease. Capillary blood sampling is being increasingly used in point-of-care testing and has been advised for obese, elderly, and other patients with fragile or inaccessible veins. The reduction of patient burden via capillary blood sampling can enable performing studies on otherwise difficult or inaccessible populations, and at greater temporal resolution. Additionally, capillary blood can be comparable to traditional venous blood draws for a variety of applications. However, to date, scRNA-seq of human capillary blood has not yet been validated nor applied to study the immune system. In order to make small volumes of capillary blood (100 ul) amenable to scRNA-seq, as described herein (including this example), a platform which consists of a painless vacuum-based blood collection device, sample de-multiplexing leveraging commercial genotype data, and an analysis pipeline used to identify time-of-day and subject specific genes was developed. The methods, systems and platforms disclosed herein enable large scale studies of immune state variation in health and disease across people, for example using small volume of blood samples and/or blood samples that are not from venous blood draws. The high-dimensional temporal transcriptome data can be paired with computational approaches to predict and understand emergence of pathological immune states. In addition, the methods, systems and platforms disclosed in make collection and profiling of human immune cells less invasive, less expensive and as such more scalable than traditional methods rooted in large venous blood draws.

Single Cell Sequencing

Disclosed herein include embodiments of a method for single cell ribonucleic acid sequencing (or single cell sequencing or profiling). In some embodiments, the method comprises providing, receiving, or causing to obtain a first low volume, capillary blood sample (or any low volume blood sample and/or any blood sample not obtained from a vein or by venipuncture) obtained from a subject at a first time point. The method can comprise diluting the first sample to obtain a first diluted sample. The method can comprise isolating first cells of interest, such as first capillary peripheral blood mononuclear cells (cPBMCs), from the first diluted sample with gradient centrifugation. The method can comprise performing sequencing, such as single cell ribonucleic acid sequencing (scRNA-seq), on the first cPBMCs isolated to generate first scRNA-seq data. The method can comprise determining a first single cell profile, such as a first scRNA profile, of the subject at the first time point using the first single cell sequencing data, such as first scRNA-seq data, and single-nucleotide polymorphisms (SNPs) of the subject.

In some embodiments, the method comprises providing, receiving, or causing to obtain a second low volume, capillary blood sample obtained (or any low volume blood sample and/or any blood sample not obtained from a vein or by venipuncture) from a subject at a second time point. The method can comprise diluting the second sample to obtain a second diluted sample. The method can comprise isolating second immune cells such as cPBMCs from the second diluted sample with gradient centrifugation. The method can comprise performing single cell sequencing, such as scRNA-seq, on the second cPBMCs isolated to generate second scRNA-seq data. The method can comprise determining a second single cell profile, such as a second scRNA profile, of the subject at the second time point using the second single cell sequencing data, such as scRNA-seq data, and SNPs of the subject.

The first time point and the second time point (or any time points when two samples are collected, whether from the same subject or from different time points) can be different or the same. In some embodiments, the first time point and the second time point (or any time points when two samples are collected, whether from the same subject or from different time points) can be, be about, be at least, be at least about, be at most, or be at most about, 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 month, 2 months, 3 months, 4 months, 5 months, 6 months, 7 months, 8 months, 9 months, 10 months, 11 months, 1 year, 2 years, 3 years, 4 years, 5 years, or a number or a range between any two of these values, apart. For example, the first time point and the second time point are about 2 hours to about 24 hours apart.

In some embodiments, the subject is in a first health state at a first time point, and the subject is in a second health state at a second time point. The first health state at the first time point can comprise a first state, such as a first disease state of a disease, and the second health state at the second time point can comprise a first state, such as a second disease state of the disease. The first health state at the first time point can comprise a state, such as a disease state of a first disease, and the second health state at the second time point can comprise a state, such as a disease state of second disease. The first state and the second state can be different. The first disease and the second disease can be different. A state or a disease can be, for example, a cancer, a non-cancer disease, Alzheimer's disease, Parkinson's Disease, dementia, rheumatoid arthritis, inflammation, pain, high blood pressure, stress, or insomnia. A state or a disease may require medical intervention. A state or a disease may not require medical intervention. The first health state at the first time point can comprise first symptoms. The second health state at the second time point can comprise second symptoms. A symptom can be, for example, fever or chills, cough, shortness of breath or difficulty breathing, fatigue, muscle or body aches, headache, loss of taste or smell, sore throat, congestion or runny nose, nausea or vomiting, or diarrhea. A symptom can be, for example, pain, weight loss without trying, fatigue, fever, changes in skin, sores that don't heal, cough or hoarseness that does not go away, unusual bleeding, or anemia. A symptom can be, for example, memory loss. The first symptoms and the second symptoms can be identical. The first symptoms and the second symptoms can be different. The first symptoms can comprise the second symptoms. The second symptoms can comprise the first symptoms. The first symptoms and the second symptoms can comprise an identical symptom of different severities. In some embodiments, the method comprises receiving the first health state of the subject at the first time point and the second health state of the subject at the second time point. In some embodiments, the method comprises correlating (e.g., performing an analysis, such as statistical analysis, or using machine learning) the first health state of the subject at the first time point with the first single cell profile, such as scRNA profile, of the subject at the first time point. The method can comprise correlating (e.g., performing an analysis, such as statistical analysis, or using machine learning) the second health state of the subject at the second time point with the second single cell profile, such as scRNA profile, of the subject at the second time point.

In some embodiments, the method comprises determining a difference between the single cell profiles of a subject at different time points, such as the scRNA profile of the subject at the first time point and the second scRNA profile of the subject at the second time point, or single cell profiles of two subjects at the same or similar time point or different time point. Any differences between two single cell profiles, such as scRNA profiles, can be performed in a reduced dimensionality space. The dimensionality of the space can be, for example, 10, 11, 12, 13, 14, 15, 16, 17, 18, 19, 20, 30, 40, 50, or more. Differences between two single cell profiles (or single cell profiles, such as mRNA expression profiles, proteomics profiles, or multiomics profiles) can be determined as described in U.S. Application Publication No. 2020/0090782, the content of which is incorporated herein by reference in its entirety. In some embodiments, the method comprises correlating (i) the difference between the scRNA profile of the subject at the first time point and the second scRNA profile of the subject at the second time point and (ii) the difference between the first health state of the subject at the first time point and the second health state of the subject at the second time point.

The method can thus be used to determine one or more genes of interest, such as those disclosed in the present disclosure or those described in Dobreva, T, et al. Single cell profiling of capillary blood enables out of clinic human immunity studies. Sci Rep 10, 20540 (2020), the content of which is incorporated herein by reference in its entirety. The one or more genes of interest can comprise diurnal genes, such as those disclosed in the present disclosure or those described in Dobreva, T, et al. The one or more genes of interest can comprise one or more genes each with a time of day variation (e.g., morning, noon, afternoon, or evening) in two single cell profiles of a subject, such as the first scRNA profile and the second scRNA profile of the subject. The method can comprise designing a gene panel comprising the one or more genes of interest. The number of genes of interest (or the number of genes that are diurnal or with time of day variation) can be different in different embodiments. In some embodiments, the number of genes of interest (or the number of genes that are diurnal or with time of day variation) is, is about, is at least, is at least about, is at most, or is at most about, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, or a number or a range between any two of these values. The number of genes (or the number of genes that are diurnal or with time of day variation) in the gene panel is different in different embodiments. In some embodiments, the number of genes in the gene panel is, is about, is at least, is at least about, is at most, or is at most about, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, or a number or a range between any two of these values. The method can comprise determining a difference between the first health state of the subject at the first time point and the second health state of the subject at the second time point.

In some embodiments, determining a single cell profile can comprise performing sample demultiplexing on single cell sequencing data. In some embodiments, determining a single cell profile can comprise determining one or more scRNA profile. Determining a first scRNA profile and/or a second scRNA profile comprises performing sample demultiplexing of the first scRNA data of the subject and/or the second scRNA data of the subject using SNPs of the subject to determine the first scRNA profile of the subject and/or the second scRNA profile of the subject. In some embodiments, performing sample demultiplexing of the first scRNA data of the subject comprises: classifying scRNA-seq reads with an identical cell label in the first scRNA data as reads generated from a sample obtained from the subject based on (i) SNPs present in one or more of the scRNA-seq reads with the identical cell label and, (ii) optionally, SNPs of the subject. SNPs in reads having a first identical cell label can be compared with SNPs in reads having a second identical cell label. If SNPs present in reads having the first cell label and the SNPs present in reads having the second cell label are identical or similar (e.g., 95%, 96%, 97%, 98%, 99%, or more), the reads are generated from two cells from one subject. If SNPs present in reads having the first cell label and the SNPs present in reads having the second cell label are dissimilar (e.g., 90%, 89%, 88%, 87%, 86%, or less), the reads are generated from two cells from two subjects. In some embodiments, performing the sample demultiplexing of the first scRNA data of the subject comprises: classifying scRNA-seq reads with an identical cell label in the second scRNA data as originating from a sample obtained from the subject based on SNPs present in one or more of the scRNA-seq reads with the identical cell label and (ii) optionally, SNPs of the subject. Reads can be classifying by performing an analysis of the reads, such as a statistical analysis, or using a machine learning model. The SNPs of the subject can be determined using the first low volume, capillary blood sample of the subject. In some embodiments, the SNPs of the subject are determined by bulk RNA sequencing and/or scRNA sequencing. Said bulk RNA sequencing and/or scRNA sequencing can be performed using a low volume, capillary blood sample (or a low volume blood sample, or a blood sample not obtained from a vein or by venipuncture) of the subject. The number of SNPs used to determine scRNA profiles (e.g., SNPs present in one or more of scRNA-seq reads or SNPs the subject has and used to determine scRNA profiles) can be different in different embodiments. In some embodiments, the number of SNPs is, is about, is at least, is at least about, is at most, or is at most about, 5, 6, 7, 8, 9, 10 20, 30, 40, 50, 60, 70, 80, 90, 100, 200, 300, 400, 500, 600, 700, 800, 900, 1000, or a number or a range between any two of these values.

Disclosed herein include embodiments of a method for single cell sequencing, such as single cell ribonucleic acid sequencing. In some embodiments, the method comprises: providing a plurality of low volume, capillary blood samples (or any low volume blood samples and/or any blood samples not obtained from veins or by venipuncture) obtained from a subject at a plurality of time points. The method can comprise, for each of the plurality of samples, diluting the sample to obtain a diluted sample. The method can comprise isolating cells of interest, such as immune cells or capillary peripheral blood mononuclear cells (cPBMCs), from the diluted sample with gradient centrifugation. The method can comprise performing single cell sequencing, such as single cell ribonucleic acid sequencing (scRNA-seq) on the cells of interest, such as immune cells or cPBMCs isolated to generate scRNA-seq data. The method can comprise determining a single cell profile, such has a scRNA profile, of the subject at the time point the sample is collected from the single cell sequencing data, such as scRNA-seq data, and single-nucleotide polymorphisms (SNPs) of the subject. The method can comprise determining one or more differences between single cell profiles, such as scRNA profiles, of the subject at two or more of the plurality of time points. Any two time points can be, be about, be at least, be at least about, be at most, or be at most about, 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 month, 2 months, 3 months, 4 months, 5 months, 6 months, 7 months, 8 months, 9 months, 10 months, 11 months, 1 year, 2 years, 3 years, 4 years, 5 years, or a number or a range between any two of these values, apart. For example, any two time points are 2 hours to about 24 hours apart. The method can thus be used to determine one or more genes of interest, such as those disclosed in the present disclosure or those described in Dobreva, T, et al. The one or more genes of interest can comprise diurnal genes, such as those disclosed in the present disclosure or those described in Dobreva, T, et al. The one or more genes of interest can comprise one or more genes each with a time of day variation (e.g., morning, noon, afternoon, or evening) in the scRNA profiles, such as those disclosed in the present disclosure or those described in Dobreva, T, et al. The method can comprise designing a gene panel comprising the one or more genes of interest.

In some embodiments, the scRNA-seq comprises a whole transcriptome RNA sequencing. The scRNA profile can comprise a whole transcriptome profile. In some embodiments, the scRNA-seq comprises a target scRNA-seq. In some embodiments, the single cell sequencing comprises ribonucleic acid (RNA) sequencing, deoxyribonucleic acid (DNA) or DNA-based sequencing (e.g., protein expression profiling), multiomics sequencing, and/or exosome sequencing. The single cell profile can comprise: an RNA expression profile, a protein expression profile, a DNA profile, a multiomics profile, and/or an exome profile. The single cell profile, such as scRNA profile, can comprise expression information (e.g., expression profiles) of a plurality of genes, such as 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, or more or fewer genes.

Disclosed herein include embodiments of a method for single cell sequencing. In some embodiments, the method comprises providing a plurality of low volume, capillary blood samples (or any low volume blood sample and/or any blood sample not obtained from a vein or by venipuncture) obtained from a plurality of subjects. Each of the plurality of samples can be obtained from a different subject. Two or more of the plurality of samples can be obtained from one subject at different time points or the same or similar time points. The method can comprise isolating immune cells from each of the plurality of samples to obtain isolated immune cells. The method can comprise pooling the isolated immune cells of the plurality of subjects to obtain pooled immune cells of the plurality of subjects. The method can comprise performing single cell sequencing on the pooled immune cells of the plurality of subjects to generate single cell sequencing data of the plurality of subjects. The method can comprise determining a single cell profile of each of the plurality of subjects using the single cell sequence data of the plurality of subjects and single-nucleotide polymorphisms (SNPs) of the plurality of subjects.

In some embodiments, the method comprises diluting the plurality of samples to obtain a plurality of diluted sample.

Isolating the immune cells from each of the plurality of samples to obtain isolated immune cells can comprise isolating the immune cells from each of the plurality of diluted samples to obtain isolated immune cells.

Disclosed herein include embodiments of a method for single cell sequencing. In some embodiments, the method comprises providing a plurality of low volume, capillary blood samples (or any low volume blood samples and/or any blood samples not obtained from veins or by venipuncture) each obtained from a plurality of subjects. The method can comprise pooling the plurality of samples to obtain a pooled sample. The method can comprise isolating immune cells from the pooled sample to obtain isolated immune cells. The method can comprise performing single cell sequencing on the pooled immune cells to generate single cell sequencing data of the plurality of subjects. The method can comprise determining a single cell profile of each of the plurality of subjects using the single cell sequence data of the plurality of subjects and single-nucleotide polymorphisms (SNPs) of the plurality of subjects.

In some embodiments, the method comprises diluting the pooled sample to obtain a diluted sample. Isolating the immune cells from the pooled sample can comprise isolating the immune cells from the diluted sample. In some embodiments, the plurality of samples is collected from the plurality of subjects within 1 day, 2 days, 3 days, 4 days, five days, 6 days, 1 week, 2 weeks, 3 weeks, 4 weeks, or 1 month, of each other. In some embodiments, samples are collected from two subjects within 1 day, 2 days, 3 days, 4 days, five days, 6 days, 1 week, 2 weeks, 3 weeks, 4 weeks, or 1 month, of each other. Sample demultiplexing based on SNPs can be used differentiate cells from different subjects without sample indexing or tagging (antibody-based or chemical-based sample indexing or tagging) of cells from different samples. In some embodiments, isolating the immune cells comprises isolating the immune cells with gradient centrifugation. In some embodiments, the immune cells comprise peripheral blood mononuclear cells (PBMCs), such as lymphocytes (T cells, B cells, NK cells) and monocytes.

In some embodiments, the single cell sequencing comprises ribonucleic acid (RNA) sequencing or profiling, deoxyribonucleic acid (DNA) sequencing or profiling, DNA-based sequencing or profiling (such as protein expression profiling), multiomics sequencing or profiling, and/or exosome sequencing. The single cell profile can comprise: an RNA expression profile, a protein expression profile, a DNA profile, a multiomics profile, and/or an exome profile.

In some embodiments, determining the single cell profile comprises performing sample demultiplexing of the single cell sequencing data of the plurality of subjects using SNPs of the plurality of subjects to determine the single cell profile of each of the plurality of subjects. In some embodiments, performing sample demultiplexing comprises classifying single cell sequencing reads with an identical cell in the single cell sequencing data as reads generated from a cell of a sample obtained from a subject based on (i) SNPs present in one or more of the single cell sequencing reads and (ii) optionally, SNPs of the one or more subjects of the plurality of subjects. Reads can be classifying by performing an analysis pf the reads, such as a statistical analysis, or using a machine learning model. SNPs in reads having a first identical cell label can be compared with SNPs in reads having a second identical cell label. If SNPs present in reads having the first cell label and the SNPs present in reads having the second cell label are identical or similar (e.g., 95%, 96%, 97%, 98%, 99%, or more), the reads are generated from two cells from one subject. If SNPs present in reads having the first cell label and the SNPs present in reads having the second cell label are dissimilar (e.g., 90%, 89%, 88%, 87%, 86%, or less), the reads are generated from two cells from two subjects. The SNPs of one or each or the one or more subject can be determined by bulk sequencing and/or single cell sequencing. Said bulk sequencing and/or single cell sequencing can be performed using a low volume, capillary blood sample (or a low volume blood sample, or a blood sample not obtained from a vein or by venipuncture) obtained from the subject. The number of SNPs used to determine single cell profiles (e.g., SNPs present in one or more of single cell sequencing reads or SNPs a subject has and used to determine single cell profiles) can be different in different embodiments. In some embodiments, the number of SNPs is, is about, is at least, is at least about, is at most, or is at most about, 5, 6, 7, 8, 9, 10 20, 30, 40, 50, 60, 70, 80, 90, 100, 200, 300, 400, 500, 600, 700, 800, 900, 1000, or a number or a range between any two of these values.

In some embodiments, a single cell profiling of a low volume, capillary blood sample of a first subject of the plurality of subjects has been performed previously. No single cell profiling of any sample or any low volume, capillary blood sample of a second subject of the plurality of subject may have been performed previously.

The volume of a sample can be different in different embodiments. In some embodiments, the volume of a sample can be, be about, be at least, be at least about, be at most, or be at most about, 10 µl, 15 µl, 20 µl, 25 µl, 30 µl, 35 µl, 40 µl, 45 µl, 50 µl, 55 µl, 60 µl, 65 µl, 70 µl, 75 µl, 80 µl, 85 µl, 90 µl, 95 µl, 100 µl, 105 µl, 110 µl, 115 µl, 120 µl, 125 µl, 130 µl, 135 µl, 140 µl, 145 µl, 150 µl, 155 µl, 160 µl, 165 µl, 170 µl, 175 µl, 180 µl, 185 µl, 190 µl, 195 µl, 200 µl, 210 µl, 220 µl, 230 µl, 240 µl, 250 µl, 260 µl, 270 µl, 280 µl, 290 µl, 300 µl, 310 µl, 320 µl, 330 µl, 340 µl, 350 µl, 360 µl, 370 µl, 380 µl, 390 µl, 400 µl, 410 µl, 420 µl, 430 µl, 440 µl, 450 µl, 460 µl, 470 µl, 480 µl, 490 µl, 500 µl, 510 µl, 520 µl, 530 µl, 540 µl, 550 µl, 560 µl, 570 µl, 580 µl, 590 µl, 600 µl, or a number or a range between any two of these values. For example, a sample (e.g., the first sample, the second sample, and/or one, one or more, or each of the plurality of samples) has a volume of about 20 µl to about 500 µl.

In some embodiments, a sample is collected by a subject from which the sample is collected from. For example, the first sample is collected by the first subject. For example, the second sample is collected by the second subject. For example, one, one or more, or each of the plurality of samples is collected by the subject from whom the sample is obtained from. In some embodiments, a sample (e.g., the first sample, the second sample, and/or one, one or more, or each of the plurality of samples) is collected in a non-clinical setting and/or out of clinic. In some embodiments, a sample (e.g., the first sample, the second sample, and/or one, or one or more, or each of the plurality of samples) is collected using a device comprising microneedles, a device comprising microfluidic channels, a push-button collection device, or a combination thereof. In some embodiments, a sample is collected from a deltoid or a finger of the subject from which the sample is collected. For example, the first sample, is collected from a deltoid of the subject at the first time point. For example, the second sample is collected from a deltoid or finger of the subject at the second time point. For example, one, one or more, or each of the plurality of samples is collected from a deltoid or a finger of a subject from which the sample is collected.

The dilution of a sample (or a pooled sample) can be different in different embodiments. In some embodiments, the dilution of a sample (or a pooled sample) is, is about, is at least, is at least about, is at most, or is at most about, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, or a number or a range between any two of these values. For example, the dilution of a sample (or a pooled sample) is about 1:2 to about 1:50. The volume of a diluted sample can be different in different embodiments. In some embodiments, the volume of a diluted sample is, is about, is at least, is at least about, is at most, or is at most about, 0.5 ml, 0.6 ml, 0.7 ml, 0.8 ml, 0.9 ml, 1 ml, 1.1 ml, 1.2 ml, 1.3 ml, 1.4 ml, 1.5 ml, 1.6 ml, 1.7 ml, 1.8 ml, 1.9 ml, 2 ml, or a number or a range between any two of these values. For example, the volume of a sample is about 100 μl, and the sample is diluted to about 1 ml.

In some embodiments, a sample is diluted using a dilution reagent. The dilution reagent comprises a buffer and/or a growth medium. The pH of the buffer (or the dilution reagent) can be different in different embodiments. In some embodiments, the pH of the buffer (or the dilution reagent) is, is about, is at least, is at least about, is at most, or is at most about, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9.0, or a number or a range between any two of these values. For example, the pH of the buffer is about 7.4. The buffer can comprise one or more components, such as salts. For example, the buffer comprises sodium chloride, potassium chloride, disodium phosphate, monopotassium phosphate, or a combination thereof. The buffer can comprise phosphate-buffered saline.

The concentration of a component of the buffer can be different in different embodiments. In some embodiments, the concentration of a component of the buffer is, is about, is at least, is at least about, is at most, or is at most about, 0.1 mmol/L, 0.2 mmol/L, 0.3 mmol/L, 0.4 mmol/L, 0.5 mmol/L, 0.6 mmol/L, 0.7 mmol/L, 0.8 mmol/L, 0.9 mmol/L, 1 mmol/L, 1.1 mmol/L, 1.2 mmol/L, 1.3 mmol/L, 1.4 mmol/L, 1.5 mmol/L, 1.6 mmol/L, 1.7 mmol/L, 1.8 mmol/L, 1.9 mmol/L, 2 mmol/L, 2.1 mmol/L, 2.2 mmol/L, 2.3 mmol/L, 2.4 mmol/L, 2.5 mmol/L, 2.6 mmol/L, 2.7 mmol/L, 2.8 mmol/L, 2.9 mmol/L, 3 mmol/L, 3.1 mmol/L, 3.2 mmol/L, 3.3 mmol/L, 3.4 mmol/L, 3.5 mmol/L, 3.6 mmol/L, 3.7 mmol/L, 3.8 mmol/L, 3.9 mmol/L, 4 mmol/L, 4.1 mmol/L, 4.2 mmol/L, 4.3 mmol/L, 4.4 mmol/L, 4.5 mmol/L, 4.6 mmol/L, 4.7 mmol/L, 4.8 mmol/L, 4.9 mmol/L, 5 mmol/L, 6 mmol/L, 7 mmol/L, 8 mmol/L, 9 mmol/L, 10 mmol/L, 11 mmol/L, 12 mmol/L, 13 mmol/L, 14 mmol/L, 15 mmol/L, 16 mmol/L, 17 mmol/L, 18 mmol/L, 19 mmol/L, 20 mmol/L, 21 mmol/L, 22 mmol/L, 23 mmol/L, 24 mmol/L, 25 mmol/L, 26 mmol/L, 27 mmol/L, 28 mmol/L, 29 mmol/L, 30 mmol/L, 31 mmol/L, 32 mmol/L, 33 mmol/L, 34 mmol/L, 35 mmol/L, 36 mmol/L, 37 mmol/L, 38 mmol/L, 39 mmol/L, 40 mmol/L, 41 mmol/L, 42 mmol/L, 43 mmol/L, 44 mmol/L, 45 mmol/L, 46 mmol/L, 47 mmol/L, 48 mmol/L, 49 mmol/L, 50 mmol/L, 51 mmol/L, 52 mmol/L, 53 mmol/L, 54 mmol/L, 55 mmol/L, 56 mmol/L, 57 mmol/L, 58 mmol/L, 59 mmol/L, 60 mmol/L, 61 mmol/L, 62 mmol/L, 63 mmol/L, 64 mmol/L, 65 mmol/L, 66 mmol/L, 67 mmol/L, 68 mmol/L, 69 mmol/L, 70 mmol/L, 71 mmol/L, 72 mmol/L, 73 mmol/L, 74 mmol/L, 75 mmol/L, 76 mmol/L, 77 mmol/L, 78 mmol/L, 79 mmol/L, 80 mmol/L, 81 mmol/L, 82 mmol/L, 83 mmol/L, 84 mmol/L, 85 mmol/L, 86 mmol/L, 87 mmol/L, 88 mmol/L, 89 mmol/L, 90 mmol/L, 91 mmol/L, 92 mmol/L, 93 mmol/L, 94 mmol/L, 95 mmol/L, 96 mmol/L, 97 mmol/L, 98 mmol/L, 99 mmol/L, 100 mmol/L, 101 mmol/L, 102 mmol/L, 103 mmol/L, 104 mmol/L, 105 mmol/L, 106 mmol/L, 107 mmol/L, 108 mmol/L, 109 mmol/L, 110 mmol/L, 111 mmol/L, 112 mmol/L, 113 mmol/L, 114 mmol/L, 115 mmol/L, 116 mmol/L, 117 mmol/L, 118 mmol/L, 119 mmol/L, 120 mmol/L, 121 mmol/L, 122 mmol/L, 123 mmol/L, 124 mmol/L, 125 mmol/L, 126 mmol/L, 127 mmol/L, 128 mmol/L, 129 mmol/L, 130 mmol/L, 131 mmol/L, 132 mmol/L, 133 mmol/L, 134 mmol/L, 135 mmol/L, 136 mmol/L, 137 mmol/L, 138 mmol/L, 139 mmol/L, 140 mmol/L, 141 mmol/L, 142 mmol/L, 143 mmol/L, 144 mmol/L, 145 mmol/L, 146 mmol/L, 147 mmol/L, 148 mmol/L, 149 mmol/L, 150 mmol/L, 151 mmol/L, 152 mmol/L, 153 mmol/L, 154 mmol/L, 155 mmol/L, 156 mmol/L, 157 mmol/L, 158 mmol/L, 159 mmol/L, 160 mmol/L, 161 mmol/L, 162 mmol/L, 163 mmol/L, 164 mmol/L, 165 mmol/L, 166 mmol/L, 167 mmol/L, 168 mmol/L, 169 mmol/L, 170 mmol/L, 171 mmol/L, 172 mmol/L, 173 mmol/L, 174 mmol/L, 175 mmol/L, 176 mmol/L, 177 mmol/L, 178 mmol/L, 179 mmol/L, 180 mmol/L, 181 mmol/L, 182 mmol/L, 183 mmol/L, 184 mmol/L, 185 mmol/L, 186 mmol/L, 187 mmol/L, 188 mmol/L, 189 mmol/L, 190 mmol/L, 191 mmol/L, 192 mmol/L, 193 mmol/L, 194 mmol/L, 195 mmol/L, 196 mmol/L, 197 mmol/L, 198 mmol/L, 199 mmol/L, 200 mmol/L, or a number or a range between any two of these values. For example, a concentration of sodium chloride can be about 137 mmol/L, a concentration of potassium chloride is about 2.7 mmol/L, a concentration of disodium phosphate is about 10 mmol/L, and/or a concentration of monopotassium phosphate is about 1.8 mmol/L. The concentration of a component of the buffer can be different in different embodiments. In some embodiments, the concentration of a component of the buffer is, is about, is at least, is at least about, is at most, or is at most about, 0.1 g/L, 0.2 g/L, 0.3 g/L, 0.4 g/L, 0.5 g/L, 0.6 g/L, 0.7 g/L, 0.8 g/L, 0.9 g/L, 1 g/L, 1.1 g/L, 1.2 g/L, 1.3 g/L, 1.4 g/L, 1.5 g/L, 1.6 g/L, 1.7 g/L, 1.8 g/L, 1.9 g/L, 2 g/L, 2.1 g/L, 2.2 g/L, 2.3 g/L, 2.4 g/L, 2.5 g/L, 2.6 g/L, 2.7 g/L, 2.8 g/L, 2.9 g/L, 3 g/L, 3.1 g/L, 3.2 g/L, 3.3 g/L, 3.4 g/L, 3.5 g/L, 3.6 g/L, 3.7 g/L, 3.8 g/L, 3.9 g/L, 4 g/L, 4.1 g/L, 4.2 g/L, 4.3 g/L, 4.4 g/L, 4.5 g/L, 4.6 g/L, 4.7 g/L, 4.8 g/L, 4.9 g/L, 5 g/L, 5.1 g/L, 5.2 g/L, 5.3 g/L, 5.4 g/L, 5.5 g/L, 5.6 g/L, 5.7 g/L, 5.8 g/L, 5.9 g/L, 6 g/L, 6.1 g/L, 6.2 g/L, 6.3 g/L, 6.4 g/L, 6.5 g/L, 6.6 g/L, 6.7 g/L, 6.8 g/L, 6.9 g/L, 7 g/L, 7.1 g/L, 7.2 g/L, 7.3 g/L, 7.4 g/L, 7.5 g/L, 7.6 g/L, 7.7 g/L, 7.8 g/L, 7.9 g/L, 8 g/L, 8.1 g/L, 8.2 g/L, 8.3 g/L, 8.4 g/L, 8.5 g/L, 8.6 g/L, 8.7 g/L, 8.8 g/L, 8.9 g/L, 9 g/L, 9.1 g/L, 9.2 g/L, 9.3 g/L, 9.4 g/L, 9.5 g/L, 9.6 g/L, 9.7 g/L, 9.8 g/L, 9.9 g/L, 10 g/L, 11 g/L, 12 g/L, 13 g/L, 14 g/L, 15 g/L, 16 g/L, 17 g/L, 18 g/L, 19 g/L, 20 g/L, 21 g/L, 22 g/L, 23 g/L, 24 g/L, 25 g/L, 26 g/L, 27 g/L, 28 g/L, 29 g/L, 30 g/L, or a number or a range between any two of these values.

In some embodiments, the growth medium comprises fetal bovine serum. The growth medium can comprise bovine serum albumin. The growth medium can comprise a serum-free medium. The growth medium can comprise a protein-free medium. The growth medium can comprise a chemically-defined medium. The growth medium can comprise a peptide-free medium. The concentration of a growth medium can be different in different embodiments. In some embodiments, the concentration of a growth medium (e.g., v/v, w/v, or w/w) can be, be about, be at least, be at least about, be at most, or be at most about, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, 5%, 5.1%, 5.2%, 5.3%, 5.4%, 5.5%, 5.6%, 5.7%, 5.8%, 5.9%, 6%, 6.1%, 6.2%, 6.3%, 6.4%, 6.5%, 6.6%, 6.7%, 6.8%, 6.9%, 7%, 7.1%, 7.2%, 7.3%, 7.4%, 7.5%, 7.6%, 7.7%, 7.8%, 7.9%, 8%, 8.1%, 8.2%, 8.3%, 8.4%, 8.5%, 8.6%, 8.7%, 8.8%, 8.9%, 9%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, or a number or a range between any two of these values. For example, t concentration of the growth medium in the dilution reagent can be about 0.1% v/v to about 10% v/v.

In some embodiments, isolating cells of interest (or immune cells or cPBMCs) comprises isolating cells of interest with gradient centrifugation. A density medium can be used for gradient centrifugation. The density of the density medium can be, be about, be at least, be at least about, be at most, or be at most about, 0.9 g/ml, 0.91 g/ml, 0.92 g/ml, 0.93 g/ml, 0.94 g/ml, 0.95 g/ml, 0.96 g/ml, 0.97 g/ml, 0.98 g/ml, 0.99 g/ml, 1 g/ml, 1.01 g/ml, 1.02 g/ml, 1.03 g/ml, 1.04 g/ml, 1.05 g/ml, 1.06 g/ml, 1.07 g/ml, 1.08 g/ml, 1.09 g/ml, 1.1 g/ml, 1.11 g/ml, 1.12 g/ml, 1.13 g/ml, 1.14 g/ml, 1.15 g/ml, 1.16 g/ml, 1.17 g/ml, 1.18 g/ml, 1.19 g/ml, 1.2 g/ml, 1.21 g/ml, 1.22 g/ml, 1.23 g/ml, 1.24 g/ml, 1.25 g/ml, 1.26 g/ml, 1.27 g/ml, 1.28 g/ml, 1.29 g/ml, 1.3 g/ml, 1.31 g/ml, 1.32 g/ml, 1.33 g/ml, 1.34 g/ml, 1.35 g/ml, 1.36 g/ml, 1.37 g/ml, 1.38 g/ml, 1.39 g/ml, 1.4 g/ml, 1.41 g/ml, 1.42 g/ml, 1.43 g/ml, 1.44 g/ml, 1.45 g/ml, 1.46 g/ml, 1.47 g/ml, 1.48 g/ml, 1.49 g/ml, 1.5 g/ml, 1.51 g/ml, 1.52 g/ml, 1.53 g/ml, 1.54 g/ml, 1.55 g/ml, 1.56 g/ml, 1.57 g/ml, 1.58 g/ml, 1.59 g/ml, 1.6 g/ml, 1.61 g/ml, 1.62 g/ml, 1.63 g/ml, 1.64 g/ml, 1.65 g/ml, 1.66 g/ml, 1.67 g/ml, 1.68 g/ml, 1.69 g/ml, 1.7 g/ml, 1.71 g/ml, 1.72 g/ml, 1.73 g/ml, 1.74 g/ml, 1.75 g/ml, 1.76 g/ml, 1.77 g/ml, 1.78 g/ml, 1.79 g/ml, 1.8 g/ml, 1.81 g/ml, 1.82 g/ml, 1.83 g/ml, 1.84 g/ml, 1.85 g/ml, 1.86 g/ml, 1.87 g/ml, 1.88 g/ml, 1.89 g/ml, 1.9 g/ml, 1.91 g/ml, 1.92 g/ml, 1.93 g/ml, 1.94 g/ml, 1.95 g/ml, 1.96 g/ml, 1.97 g/ml, 1.98 g/ml, 1.99 g/ml, 2 g/ml. For example, the density of the density medium is about 1 g/ml to about 1.5 g/ml.

The duration of the density centrifugation can be different in different embodiments. In some embodiments, the duration of the density centrifugation is, is about, is at least, is at least about, is at most, or is at most about, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, or a number or a range between any two of these values. For example, the duration of the density centrifugation is about 10 mins to about 30 mins.

The speed of the density centrifugation can be different in different embodiments. The speed of the density centrifugation can be, be about, be at least, be at least about, be at most, or be at most about, 400 RPM, 450 RPM, 500 RPM, 550 RPM, 600 RPM, 650 RPM, 700 RPM, 750 RPM, 800 RPM, 850 RPM, 900 RPM, 950 RPM, 1000 RPM, 1050 RPM, 1100 RPM, 1150 RPM, 1200 RPM, 1250 RPM, 1300 RPM, 1350 RPM, 1400 RPM, 1450 RPM, 1500 RPM, 1550 RPM, 1600 RPM, 1650 RPM, 1700 RPM, 1750 RPM, 1800 RPM, 1850 RPM, 1900 RPM, 1950 RPM, 2000 RPM, or a number or a range between any two of these values. For example, the speed of the density centrifugation is about 500 RPM to about 1500 RPM. In some embodiments, isolating cells of interest comprises removing a layer after gradient centrifugation comprising the cells of interest (e.g., immune cells or cPBMCs)

The volume of the layer with cells of interest and removed can be different in different embodiments. In some embodiments, the volume of the layer with cells of interest and removed is, is about, is at least, is at least about, is at most, or is at most about, 400 µl, 410 µl, 420 µl, 430 µl, 440 µl, 450 µl, 460 µl, 470 µl, 480 µl, 490 µl, 500 µl, 510 µl, 520 µl, 530 µl, 540 µl, 550 µl, 560 µl, 570 µl, 580 µl, 590 µl, 600 µl, 610 µl, 620 µl, 630 µl, 640 µl, 650 µl, 660 µl, 670 µl, 680 µl, 690 µl, 700 µl, 710 µl, 720 µl, 730 µl, 740 µl, 750 µl, 760 µl, 770 µl, 780 µl, 790 µl, 800 µl, 810 µl, 820 µl, 830 µl, 840 µl, 850 µl, 860 µl, 870 µl, 880 µl, 890 µl, 900 µl, 910 µl, 920 µl, 930 µl, 940 µl, 950 µl, 960 µl, 970 µl, 980 µl, 990 µl, 1000 µl, 1050 µl, 1100 µl, 1150 µl, 1200 µl, 1250 µl, 1300 µl, 1350 µl, 1400 µl, 1450 µl, 1500 µl, 1550 µl, 1600 µl, 1650 µl, 1700 µl, 1750 µl, 1800 µl, 1850 µl, 1900 µl, 1950 µl, 2000 µl, or a number or a range between any two of these values. For example, the volume of the layer with cells of interest removed is about 500 µl to about 1500 µl. Isolating cells of interest can comprise removing red blood cells from the layer with cells of interest and removed. Removing the red blood cells from the layer with cells of interest and removed can comprises lysing the red blood cells.

In some embodiments, the method of single cell sequencing comprises performing cell typing. The method can comprise performing diurnal gene detection. The method can comprise performing subject specific gene detection. The method can comprise performing cell type specific gene detection. The method can comprise performing pathway enrichment analysis.

Disclosed herein include embodiments of one or more reagents (e.g., a dilution reagent) or devices (e.g., a device for collecting capillary blood) for performing any method of the disclosure. The present disclosure also provides embodiments of a kit comprising one or more reagents for performing any method of the disclosure.

Matching

Disclosed herein include embodiments of a method of matching single cell profiles, such as scRNA profiles. In some embodiments, a system can perform the matching method. In some embodiments, the system comprises non-transitory memory configured to store executable instructions; and a processor (e.g., a hardware processor or a virtual processor) in communication with the non-transitory memory, the hardware processor programmed by the executable instructions to perform the matching method. The method can include receiving a profile comprising a single cell profile, such as a single cell ribonucleic acid (scRNA) profile, of each of a plurality of subjects determined using any of any method of the present disclosure. The method can include matching a first single cell profile, such as a first scRNA profile, of a first subject of the plurality of subjects determined from a first sample obtained at a first time point and a second single cell profile, such as a second scRNA profile, of a second subject of the plurality of subjects determined from a second sample obtained at a second time point. The first time point can be prior to the second time point. A first profile of the first subject can comprise a first action performed by the first subject and a first associated outcome occurred subsequent to the action being performed.

The method can include generating a report or an output (e.g., a file or a visual output) comprising the second single cell profile, such as the second scRNA profile, the first action performed by the first subject, the first associated outcome, representations (e.g., visual representations and/or non-visual representations) of one or more of the preceding, or a combination thereof. The method can include displaying or causing to display the report or the output.

In some embodiments, a system for matching single cell profiles can perform a matching method. The system can comprise non-transitory memory configured to store executable instructions and a reference profile comprising a reference single cell profile of each of a plurality of reference subjects determined whether using any method of the disclosure. The reference profile of the reference subject can comprise a reference action performed by the reference subject and an associated reference outcome occurred subsequent to the action being performed. The method can include receiving a test single cell profile of a test subject determined using any method of the disclosure. The method can include matching the test single cell profile of the test subject to a reference profile of one of the plurality of reference subjects. The matching method can include generating a report or an output (e.g., a file, or a visual output) comprising the test single cell profile, the reference action performed by the reference subject whose reference single cell profile is matched to the test single cell profile, the associated reference outcome, representations (e.g., visual representations and/or non-visual representations) of one or more of the preceding, or a combination thereof. The method can include displaying or causing to display the report or the output.

In some embodiments, a system for matching single cell profiles can perform a matching method. The system can comprise: non-transitory memory configured to store executable instructions and a reference profile comprising a reference single cell profile of each of a plurality of reference subjects determined whether using any method of the disclosure. The reference profile of the reference subject can comprise a reference action performed by the reference subject and an associated reference outcome occurred subsequent to the action being performed. The method can include receiving a test single cell profile of a test subject determined using any method of the disclosure. The method can include matching the test single cell profile of the test subject to one or more references profile of one or more of the plurality of reference subjects. The method can include generating a report or an output (e.g., a file, or a visual output) comprising the test single cell profile, the reference action performed by each of the reference subjects whose reference single cell profiles are matched to the test single cell profile, and/or the associated reference outcomes. The method can include displaying or causing to display the report or the output.

In some embodiments, the method can include receiving an action of the test subject and an associated test outcome. The method can include storing the action of the test subject and the associated test outcome in the non-transitory memory. Matching can be performed using supervised learning, unsupervised learning, or a combination thereof. Matching can be performed using a machine learning model.

In some embodiments, the action comprises a medical action, such as taking a prescription drug or a non-prescription drug or a surgical intervention. The action can comprise a non-medical action, such as lifestyle changes and self-care to promote wellness (e.g., diet, exercise, psychotherapy, relationship and spiritual counseling). An action can include one or more alternative therapies (e.g., acupuncture, chiropractic care, homeopathy, massage therapy, naturopathy). The action can be lack of action or inaction. In some embodiments, the outcome can include a change in health positively or negatively. A change in health can be a chance in physical health, intellectual health, emotional health, social health, and/or mental health. The outcome can comprise a positive health outcome, such as no or decrease in physical illness, disease, injury, mental stress, wellness, pain and discomfort. A positive health outcome can include achieving and maintaining a healthy lifestyle by being physically fit and having good mental health. In some embodiments, the outcome comprises a negative health outcome, such as presence or increase in physical illness, disease, injury, mental stress, wellness pain and discomfort.

Machine Learning Model

Machine learning models can be used with any method of the present disclosure, such as sample demultiplexing, matching single cell profiles, determining differences in single cell profiles. Non-limiting examples of machine learning models includes scale-invariant feature transform (SIFT), speeded up robust features (SURF), oriented FAST and rotated BRIEF (ORB), binary robust invariant scalable keypoints (BRISK), fast retina keypoint (FREAK), Viola-Jones algorithm, Eigenfaces approach, Lucas-Kanade algorithm, Horn-Schunk algorithm, Mean-shift algorithm, visual simultaneous location and mapping (vSLAM) techniques, a sequential Bayesian estimator (e.g., Kalman filter, extended Kalman filter, etc.), bundle adjustment, adaptive thresholding (and other thresholding techniques), Iterative Closest Point (ICP), Semi Global Matching (SGM), Semi Global Block Matching (SGBM), Feature Point Histograms, various machine learning algorithms (such as e.g., support vector machine, k-nearest neighbors algorithm, Naive Bayes, neural network (including convolutional or deep neural networks), or other supervised/unsupervised models, etc.), and so forth.

Once trained, a machine learning model can be stored in a computing system (e.g., the computing system 1000 described with reference to FIG. 10). Some examples of machine learning models can include supervised or non-supervised machine learning, including regression models (such as, for example, Ordinary Least Squares Regression), instance-based models (such as, for example, Learning Vector Quantization), decision tree models (such as, for example, classification and regression trees), Bayesian models (such as, for example, Naive Bayes), clustering models (such as, for example, k-means clustering), association rule learning models (such as, for example, a-priori models), artificial neural network models (such as, for example, Perceptron), deep learning models (such as, for example, Deep Boltzmann Machine, or deep neural network), dimensionality reduction models (such as, for example, Principal Component Analysis), ensemble models (such as, for example, Stacked Generalization), and/or other machine learning models.

A layer of a neural network (NN), such as a deep neural network (DNN) can apply a linear or non-linear transformation to its input to generate its output. A neural network layer can be a normalization layer, a convolutional layer, a softsign layer, a rectified linear layer, a concatenation layer, a pooling layer, a recurrent layer, an inception-like layer, or any combination thereof. The normalization layer can normalize the brightness of its input to generate its output with, for example, L2 normalization. The normalization layer can, for example, normalize the brightness of a plurality of images with respect to one another at once to generate a plurality of normalized images as its output. Non-limiting examples of methods for normalizing brightness include local contrast normalization (LCN) or local response normalization (LRN). Local contrast normalization can normalize the contrast of an image non-linearly by normalizing local regions of the image on a per pixel basis to have a mean of zero and a variance of one (or other values of mean and variance). Local response normalization can normalize an image over local input regions to have a mean of zero and a variance of one (or other values of mean and variance). The normalization layer may speed up the training process.

A convolutional neural network (CNN) can be a NN with one or more convolutional layers, such as, 5, 6, 7, 8, 9, 10, or more. The convolutional layer can apply a set of kernels that convolve its input to generate its output. The softsign layer can apply a softsign function to its input. The softsign function (softsign(x)) can be, for example, (x/(1+|x|)). The softsign layer may neglect impact of per-element outliers. The rectified linear layer can be a rectified linear layer unit (ReLU) or a parameterized rectified linear layer unit (PReLU). The ReLU layer can apply a ReLU function to its input to generate its output. The ReLU function ReLU(x) can be, for example, max(0, x). The PReLU layer can apply a PReLU function to its input to generate its output. The PReLU function PReLU(x) can be, for example, x if x≥0 and ax if x<0, where a is a positive number. The concatenation layer can concatenate its input to generate its output. For example, the concatenation layer can concatenate four 5×5 images to generate one 20×20 image. The pooling layer can apply a pooling function which down samples its input to generate its output. For example, the pooling layer can down sample a 20×20 image into a 10×10 image. Non-limiting examples of the pooling function include maximum pooling, average pooling, or minimum pooling.

At a time point t, the recurrent layer can compute a hidden state s(t), and a recurrent connection can provide the hidden state s(t) at time t to the recurrent layer as an input at a subsequent time point t+1. The recurrent layer can compute its output at time t+1 based on the hidden state s(t) at time t. For example, the recurrent layer can apply the softsign function to the hidden state s(t) at time t to compute its output at time t+1. The hidden state of the recurrent layer at time t+1 has as its input the hidden state s(t) of the recurrent layer at time t. The recurrent layer can compute the hidden state s(t+1) by applying, for example, a ReLU function to its input. The inception-like layer can include one or more of the normalization layer, the convolutional layer, the softsign layer, the rectified linear layer such as the ReLU layer and the PReLU layer, the concatenation layer, the pooling layer, or any combination thereof.

The number of layers in the NN can be different in different implementations. For example, the number of layers in a NN can be 10, 20, 30, 40, or more. For example, the number of layers in the DNN can be 50, 100, 200, or more. The input type of a deep neural network layer can be different in different implementations. For example, a layer can receive the outputs of a number of layers as its input. The input of a layer can include the outputs of five layers. As another example, the input of a layer can include 1% of the layers of the NN. The output of a layer can be the inputs of a number of layers. For example, the output of a layer can be used as the inputs of five layers. As another example, the output of a layer can be used as the inputs of 1% of the layers of the NN.

The input size or the output size of a layer can be quite large. The input size or the output size of a layer can be n×m, where n denotes the width and m denotes the height of the input or the output. For example, n or m can be 11, 21, 31, or more. The channel sizes of the input or the output of a layer can be different in different implementations. For example, the channel size of the input or the output of a layer can be 4, 16, 32, 64, 128, or more. The kernel size of a layer can be different in different implementations. For example, the kernel size can be n×m, where n denotes the width and m denotes the height of the kernel. For example, n or m can be 5, 7, 9, or more. The stride size of a layer can be different in different implementations. For example, the stride size of a deep neural network layer can be 3, 5, 7 or more.

In some embodiments, a NN can refer to a plurality of NNs that together compute an output of the NN. Different NNs of the plurality of NNs can be trained for different tasks. A processor (e.g., a processor of the computing system 1000 descried with reference to FIG. 10) can compute outputs of NNs of the plurality of NNs to determine an output of the NN. For example, an output of a NN of the plurality of NNs can include a likelihood score. The processor can determine the output of the NN including the plurality of NNs based on the likelihood scores of the outputs of different NNs of the plurality of NNs.

Execution Environment

Figure 10:
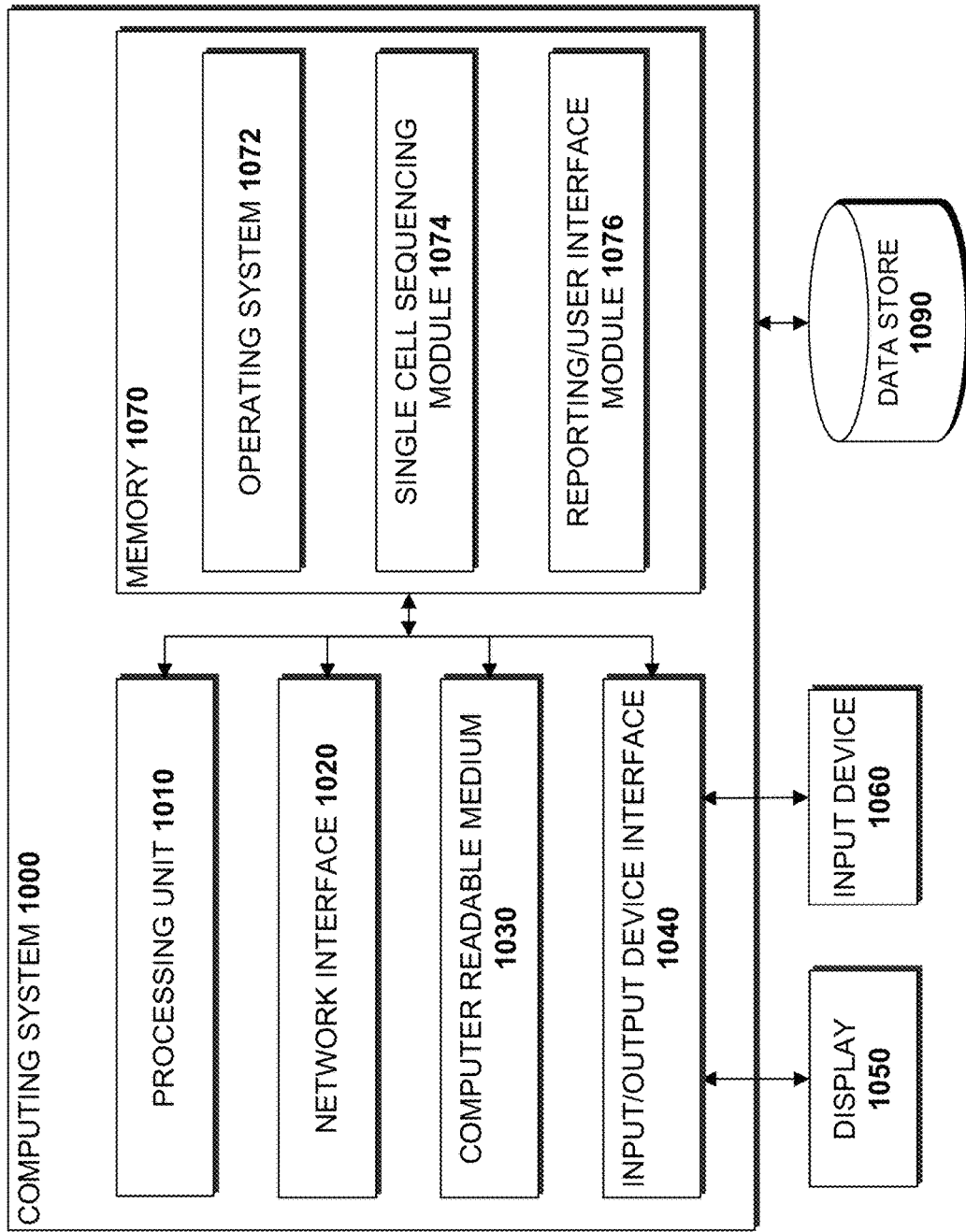
FIG. 10 is a block diagram of an illustrative computing system configured to implement any method of the present disclosure.

FIG. 10 depicts a general architecture of an example computing device 1000 that can be used in some embodiments to execute the processes and implement the features described herein. The general architecture of the computing device 1000 depicted in FIG. 10 includes an arrangement of computer hardware and software components. The computing device 1000 may include many more (or fewer) elements than those shown in FIG. 10. It is not necessary, however, that all of these generally conventional elements be shown in order to provide an enabling disclosure. As illustrated, the computing device 1000 includes a processing unit 1010, a network interface 1020, a computer readable medium drive 1030, an input/output device interface 1040, a display 1050, and an input device 1060, all of which may communicate with one another by way of a communication bus. The network interface 1020 may provide connectivity to one or more networks or computing systems. The processing unit 1010 may thus receive information and instructions from other computing systems or services via a network. The processing unit 1010 may also communicate to and from memory 1070 and further provide output information for an optional display 1050 via the input/output device interface 1040. The input/output device interface 1040 may also accept input from the optional input device 1060, such as a keyboard, mouse, digital pen, microphone, touch screen, gesture recognition system, voice recognition system, gamepad, accelerometer, gyroscope, or other input device.

The memory 1070 may contain computer program instructions (grouped as modules or components in some embodiments) that the processing unit 1010 executes in order to implement one or more embodiments. The memory 1070 generally includes RAM, ROM and/or other persistent, auxiliary or non-transitory computer-readable media. The memory 1070 may store an operating system 1072 that provides computer program instructions for use by the processing unit 1010 in the general administration and operation of the computing device 1000. The memory 1070 may further include computer program instructions and other information for implementing aspects of the present disclosure.

For example, in one embodiment, the memory 1070 includes a single cell sequencing module 1074 for performing single cell sequencing, processing single cell sequencing data, generating single cell profiles, and/or analyzing, matching, and/or differentiating single cell profiles. The memory 1070 may additionally or alternatively include a reporting or user interface module 1076 for generating, outputting, and/or displaying results of the present disclosure, such as results of single cell sequencing, single cell sequencing data, single cell profiles, and matched single cell profiles, and actions by subjects, and associated outcomes. In addition, memory 1070 may include or communicate with the data store 1090 and/or one or more other data stores that store single cell sequencing data, single cell profiles, and/or actions performed by subjects and associated outcomes.

EXAMPLES

Some aspects of the embodiments discussed above are disclosed in further detail in the following examples, which are not in any way intended to limit the scope of the present disclosure.

Example 1

Single Cell Profiling of Capillary Blood Enables Out of Clinic Human Immunity Studies This example demonstrates that capillary blood can be used for collection and profiling of human immune cells, which is less invasive, less expensive and more scalable than the traditional methods relying on large venous blood draws.

Methods

Human Study Cohort: Four healthy adults (2 male, 2 female) were recruited (Table 3). All participants provided written informed consent. The blood collection took place in a non-BSL room to make sure the subjects were not exposed to pathogens. Subject blood was collected roughly 8 hours apart over three consecutive days.

CPBMC isolation: 100 µl of capillary blood was collected via push-button collection device (TAP from Seventh Sense Biosystems). For each blood draw, the site of collection was disinfected with an alcohol wipe and the TAP device was placed on the deltoid of the subject per device usage instructions. The button was pushed, and then blood was collected for 2-7 minutes until the indicator turned red. Blood was extracted from the TAP device by gently breaking the seal foil, and mixed with PBS+2% FBS to 1 ml. The mixture was slowly added to the side of a SepMate tube (SepMate-15 IVD, Stem Cell Technologies) containing 4.5 ml of Lymphoprep (#07811, Stem Cell Technologies) and centrifuged for 20 minutes at 800 RPM. Approximately 900 µl of CPBMC layer was extracted below the plasma layer. To further remove red blood cells, 100 µl of red blood cell lysis buffer (eBioscience 10×RBC Lysis Buffer, #00-4300-54) was added to the CPBMCs and incubated at RT for 15 minutes. The CPBMC pellet was washed twice with PBS and centrifuged at 400 rpm for 5 minutes. Cells were counted using trypan blue via an automated detector (Countess II Automated Cell Counter) and subjects' cells were pooled together for subsequent single-cell RNA sequencing.

Single-cell RNA sequencing: Subject pooled single-cell suspensions were loaded onto a Chromium Single Cell Chip (10× Genomics) based on manufacturer's instructions (targeted 10,000 cells per sample, 2,500 cells per person per time point). Captured mRNA was barcoded during cDNA synthesis and pooled for Illumina sequencing (Chromium Single Cell 3' solution—10× Genomics). Each time point was barcoded with a unique Illumina sample index, and then pooled together for sequencing in a single Illumina flow cell. The libraries were sequenced with an 8-base index read, 26-base read 1 containing cell-identifying barcodes and unique molecular identifiers (UMIs), and a 91-base read 2 containing transcript sequences on a NovaSeq 6000.

Single-cell Dataset Generation: FASTQ files from Illumina were demultiplexed and aligned using Cell Ranger v3.0 (support.10xgenomics.com/single-cell-gene-expression/software/pipelines/latest/what-is-cell-ranger, the content of which is incorporated herein by reference in its entirety) and the hg19 (human) reference genome with all options set to their defaults.

Sample Demultiplexing: FASTQ files from the single-cell sequencing Illumina libraries were aligned against the hg19 (human) reference genome using Cellranger v3.0 count function. SNPs were detected in the aligned data using freebayes (github.com/ekg/freebayes, the content of which is incorporated herein by reference in its entirety), which creates a combined variant call format (VCF) file, one per sample. SNPs were then grouped by cell barcode using popscle dsc-pileup (github.com/statgen/popscle, the content of which is incorporated herein by reference in its entirety). The SNP files for all samples were then merged into a single dsc-pileup file, and cell barcodes were disambiguated by providing a unique identifier per sample. Freemuxlet (popscle freemuxlet) was then run with default parameters to group cells into 4 subjects. This generates a probability of whether each cell barcode belongs to each subject, given the detection of single nucleotide polymorphism (SNPs) in reads associated with that cell barcode. Each cell was then assigned to the subject with the highest probability. Cells with low confidence (ambiguous cells) and high confidence in more than one subject (multiplets) were discarded, using popscle's default confidence thresholds.

Debris Removal: The raw cell gene matrix provided by Cell Ranger contains gene counts for all barcodes present in the data. To remove barcodes representing empty or debris-containing droplets, a debris removal step was performed and the statistics for debris removal pipe is shown in Table 6. First, a UMI count threshold was determined that yielded more than the expected number of cells based on original cell counts (15,000). All barcodes below this threshold were discarded. For the remaining barcodes, principal component analysis (PCA) was performed on the log-transformed cell gene matrix, and agglomerative clustering was used to cluster the cells. The number of clusters was automatically determined by minimizing the silhouette score among a range of numbers of clusters (6 to 15). For each cluster, a barcode dropoff trace was calculated by determining the number of barcodes remaining in the cluster for all thresholds in increments of 50. These cluster traces were then clustered into two clusters using agglomerative clustering—the two clusters representing "debris" with high barcode dropoff rates and "cells" with low barcode drop-off rates. All clusters categorized as "debris" were then removed from the data.

Gene Filtering: Before cell typing, genes that have a maximum count less than 3 are discarded. Furthermore, after cell typing, any genes that are not present in at least 10% of one or more cell types are discarded.

Data Normalization: Gene counts were normalized by dividing the number of times a particular gene appears in a cell (gene cell count) by the total gene counts in that cell. Furthermore, for visualization only, the gene counts were multiplied by a constant factor (5000), and a constant value of 1 was added to avoid zeros and then log transformed.

Figure 4:
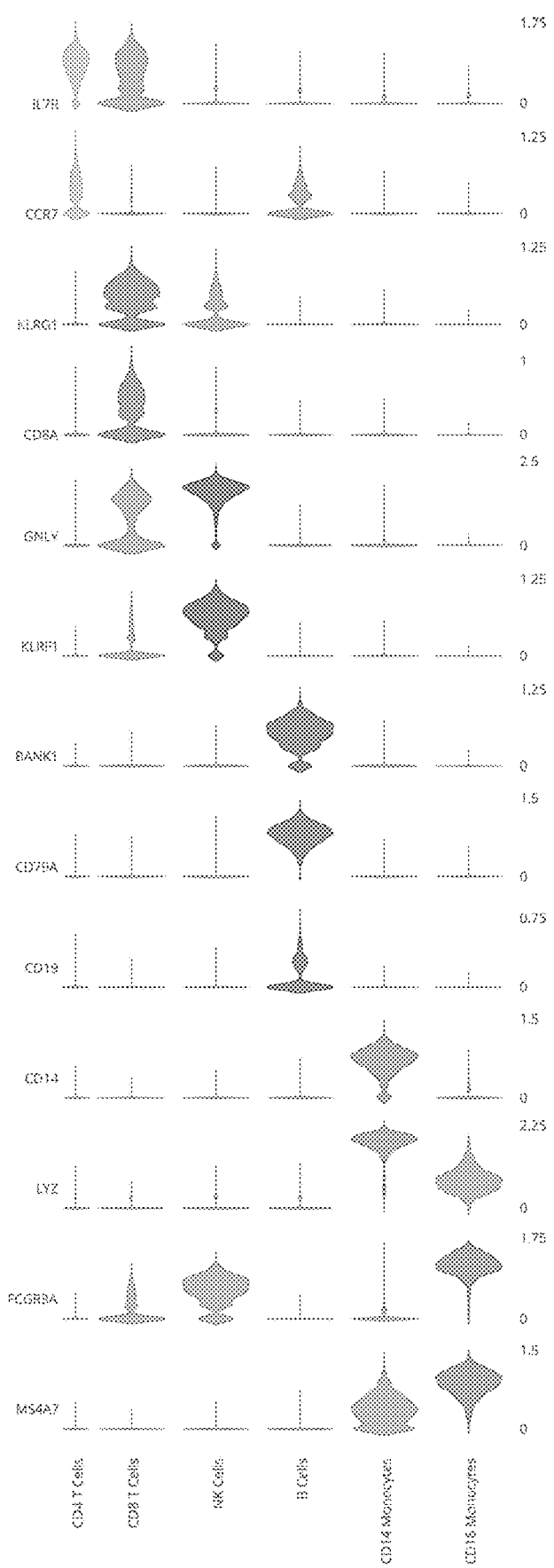
FIG. 4 shows cell type marker gene expression in cell clusters Violin plots of log-normalized gene expression (y-axis, right hand side) for cell type markers (y-axis, left hand side) used to annotate cell clusters (x-axis) for known cell types. The colors correlate to clusters from FIG. 1D.

Cell Typing: Single cell Variational Inference (scVI) was used to transform the raw cell gene expression data into a 10-dimensional variational autoencoder latent space. The variational autoencoder is conditioned on sample batch, creating a latent space which is independent of any batch-specific effects. The variational auto-encoder parameters: learning rate=1e−3, number of epochs=50 Agglomerative clustering (sci-kit learn) was used to generate clusters from the latent cell gene expression data. These clusters were then annotated based on known cell type marker genes (FIG. 4).

In order to resolve specific cell subtypes, such as those of T cells and Monocytes, 13-15 clusters were specified as an input for agglomerative clustering. Each study was started at 13 clusters and incremented until all 4 major cell types and 2 subtypes were separable. In cases where agglomerative clustering yielded multiple clusters of the same cell type, these clusters were merged into a single cell type for analysis.

Venous and Capillary Blood Comparison: In order to compare venous blood cell type distributions to capillary blood, raw gene count data was downloaded from each of the respective studies, and we performed the same cell typing pipeline as for our capillary data, first projecting the data into a latent space via scVI, followed by agglomerative clustering and manual annotation based on known cell type marker genes.

Diurnal Gene Detection: To identify genes that exhibit diurnal variation in distinct cell types, a statistical procedure was developed to detect robust gene expression differences between morning (AM) and evening (PM) samples. Given that gene expression is different between subjects, the mean gene expression within each subject was normalized for each cell type.

$$\mu'_{g_i,s_j,c_n,k} = \mu_{g_i,s_j,c_n,k} - \left( \frac{\sum_{k=1}^{N_{s_j}} 1_{k \in AM} \mu_{g_i,s_j,c_n,k}}{2\sum_{k=1}^{N_{s_j}} 1_{k \in AM}} + \frac{\sum_{k=1}^{N_{s_j}} 1_{k \in PM} \mu_{g_i,s_j,c_n,k}}{2\sum_{k=1}^{N_{s_j}} 1_{k \in PM}} \right) \quad \text{(Eq. 1)}$$

The mean gene expression μ was taken for each gene $g_i$ in all samples k for cell type $c_n$ and subject $s_j$ and renormalize it into μ' by subtracting the equally weighted mean of AM and PM samples (Eq. 1). The mean gene values were then split into an AM group and a PM group and perform a statistical test (two-tailed student-t test) to determine whether to reject the null hypothesis that gene expression in AM and PM samples come from the same distribution. Benjamini-Hochberg multiple comparison correction was performed at an FDR of 0.05 on all gene and cell type p-values to determine where to plot the significance threshold. For plotting the genes, the Z-statistic corresponding to the minimum p-value among cell types for that gene was chosen. To determine diurnality at the population level, the procedure above was repeated with all cells pooled into a single cell type.

Subject and Cell Type Specific Gene Detection: To classify genes as subject specific, genes with mean gene expression levels that are robustly different between subjects in at least one cell type were detected. For each cell type $c_n$ and gene $g_i$, subject groups containing the mean gene expression values were created from each sample. To determine whether the gene expression means from the different subjects do not originate from the same distribution, an ANOVA one-way test was performed to get an F-statistic and p-value for each gene. Benjamini-Hochberg multiple comparison correction was then performed at an FDR of 0.05 on all gene and cell type p-values. For plotting the genes, the F-statistic corresponding to the minimum p-value among cell types was chosen for that gene.

For determining gene cell type specificity, a similar procedure was performed. In particular, for each gene $g_i$, cell type groups containing the mean gene expression values for that cell type were created from each sample. A one-way ANOVA, and Benjamini-Hochberg multiple comparison correction were performed at an FDR of 0.05.

Pathway Enrichment Analysis: Pathways from the KEGG database (python bioservices package) were used to calculate pathway enrichment for genes that were among the top 250 most diurnal and individual specific. All remaining genes present in the data were considered background. In order to normalize for gene presence across pathways, each gene was weighted by dividing the number of pathways in which that gene appears. For each KEGG pathway, the test statistic for a two-proportion z-test (python statsmodel v0.11.1) is used to determine pathway enrichment. From the top level pathway classes, "Diseases" were broken out into "Other", "Immune Diseases", and "Infectious Diseases" and separated "Immune System" from "Organismal System" to understand diurnal and subject-specific genes in an immune relevant context.

Results:

Platform for low-cost interrogation of single-cell immune gene expression profiles: The platform disclosed in the present example comprises a protocol for isolating capillary peripheral blood mononuclear cells (CPBMCs) using a touch activated phlebotomy device (TAP), pooling samples to reduce per-sample cost using genome-based demultiplexing, and a computational package that leverages repeated sampling to identify genes that are differentially expressed in individuals or between time points, within subpopulations of cells (FIG. 1A). Using a painless vacuum-based blood collection device such as the commercial FDA-approved TAP to collect capillary blood makes it convenient to perform at-home self-collected sampling and removes the need for a trained phlebotomist, increasing the ease of acquiring more samples. The isolation of CPBMCs is done using gradient centrifugation and red blood cells are further removed via a red blood cell lysis buffer. The cells from the different subjects are pooled, sequenced via scRNA-seq using a single reagent kit, and demultiplexed via each subject's single-nucleotide polymorphisms (SNPs), reducing the per-sample processing cost. By pooling the data across all 6 time points, and using a genotype-free demultiplexing software (popscle), the platform was used to identify which cells belonged to which subject across time points, removing the need for a separate genotyping assay to link subjects together across batches.

Single-cell RNA sequencing (scRNA-seq) of low volume capillary blood recovers distinct immune cell populations stably across time: scRNA-seq of capillary blood platform was used to identify genes that exhibit diurnal behavior in subpopulations of cells and find subject-specific immune relevant gene signatures. A three-day study were performed, in which capillary blood was processed from four subjects in the morning and afternoon, totaling 24,087 cells across 22 samples (FIG. 1B). Major immune cell types such as T cells (CD4+, CD8+), Natural Killer cells, Monocytes (CD14+, CD16+), and B cells are present in all subjects and time points with stable expression of key marker genes (FIG. 1D, FIG. 4), demonstrating that these signals are robust to technical and biological variability of CPBMC sampling (FIG. 1C). In order to compare cell type distributions derived from our method with venous blood draws, data from 11 healthy subjects provided by three independent studies were used (Table 4).

CD14+ Monocytes make up a higher percentage of PBMCs in venous blood (n=11) versus capillary blood (n=22) (FDR<0.05, 2-sided student t-test, multiple comparison corrected), while other cell types do not have a significant difference in distributions (FIG. 1E).

High frequency scRNA-seq unveils new diurnal cell type-specific genes: Genes driven by time-of-day expression, such as those involved in leukocyte recruitment and regulation of oxidative stress, have been determined to play an important role in both innate and adaptive immune cells. Medical conditions such as atherosclerosis, parasite infection, sepsis, and allergies display distinct time-of-day immune responses in leukocytes, suggesting the presence of diurnally expressing genes that could be candidates for optimizing therapeutic efficacy via time-of-day dependent administration. However, studies examining diurnal gene expression in human blood have been limited to whole blood gene panels via qPCR, or bulk RNA-seq.

Using the platform which enables single-cell studies of temporal human immune gene expression, 395 genes (FDR<0.05, multiple comparison corrected) exhibiting diurnal activity within at least one cell subpopulation were detected (FIG. 2A). Among the 20 top diurnally classified genes, it was found that 40% of those genes were previously correlated with circadian behavior (Table 1), such as DDIT4 (FIG. 2B), SMAP2, and PCPB1. However, only 119/395 (30.1%) of these genes were detected as diurnal at the whole population level (FDR<0.05, multiple comparison corrected), suggesting there may be many more diurnally-varying genes than previously discovered. For example, IFI16 and LSP1 (FIG. 2C) have diurnal expression only in NK cells and B cells, respectively, and display previously unreported transcriptional diurnal patterns. In particular, LSP1 has been implicated in numerous leukemias and lymphomas of B cell origin. Given previous evidence of increased efficacy of time-dependent chemotherapy administration and tumor cells exhibiting out-of-sync behavior compared to normal cells, understanding LSP1's diurnal expression pattern can potentially guide timely administration of candidate therapeutics. Out of the identified 395 diurnally-varying genes, 114 (29%) are considered druggable under the drug gene interaction database (dgidb.org).

scRNA-seq profiling distinguishes diurnal gene expression from cell type abundance changes: 406 genes (FDR<0.05, multiple comparison corrected) exhibiting diurnal behavior when analyzed at the population level, such as EAF2, that do not display diurnal variation in any of our major cell types were also detected (FIG. 2D, panel i). Such false positives may come from diurnal shifts in cell type abundance rather than up- or down-regulation of genes. In the case of EAF2, which is most abundant in B cells. Without being bound by any particular theory, it is believed that the diurnality detected at the population level was a result of an increase of B cell abundance in the afternoon, and verified this in our data (p=$7.5 \times 10^{-3}$, one-sided student-t test) (FIG. 2D, panel ii). This finding highlights the importance of looking at expression within multiple cell types to avoid potentially misleading mechanistic hypotheses.

Individuals exhibit robust cell type-specific differences in genes and pathways relevant to immune function: Gene expression studies of isolated cell subpopulations across large cohorts of people have revealed a high degree of variability between individuals that cannot be accounted for by genetics alone, with environmental effects that vary over time likely playing a critical role. Furthermore, these transcriptomic differences have been linked to a wide range of therapeutic responses, such as drug-induced cardiotoxicity. However, while immune system composition and expression has been shown to be stable over long time periods within an individual, acute immune responses generate dramatic immune system changes, meaning that large single time point population studies are unable to establish whether variability between individuals is stable or the result of dynamic response to stimuli.

To probe the stability of individual gene expression signatures at the single-cell level, genes whose variation in gene expression is most likely caused by intrinsic intersubject differences rather than high frequency immune system variability was identified. The mean gene expressions of all time points were compared between subjects in all cell types and identified 1284 genes (FDR<0.05, multiple comparison corrected) that are differentially expressed in at least one subpopulation of cells. It was found that MHC class II genes, such as HLA-DRB1, HLA-E, and HLA-DRA (FIG. 3A), is among the largest sources of variation between subjects. Additionally, it was found that DDX17, which was classified previously as a gene with high intersubject variability, but low intrasubject variability via repeat sampling over longer time scales, may be a new class of temporally varying gene that varies by day of week, having consistently increasing expression each subsequent sampling day. This stresses the importance of high frequency sampling for identifying genes with the most intrinsic interindividual variability.

Figure 3B:
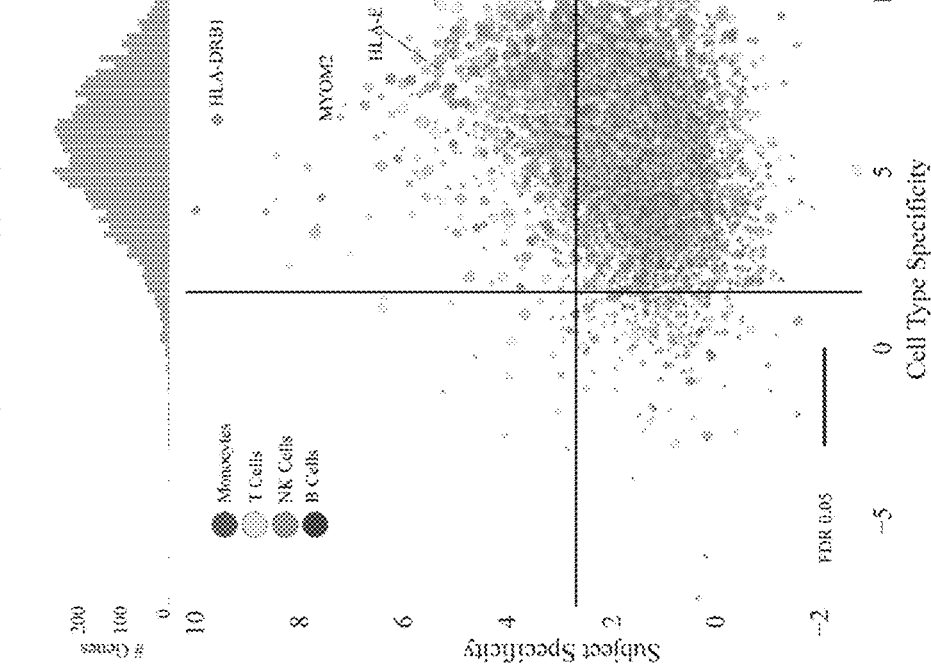
Figure 3C:
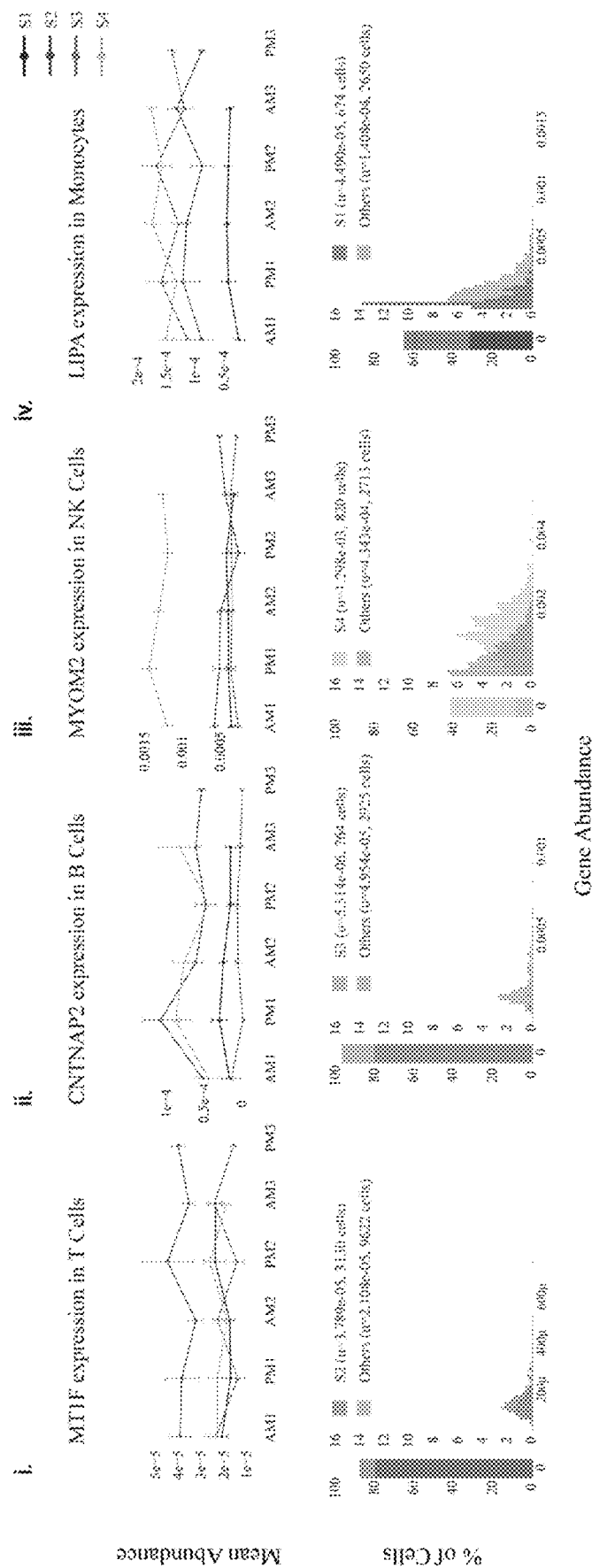

Numerous subject-specific genes are revealed in specific immune cell types: Within the 1284 genes with intrinsic interindividual variability, myriad disease-relevant genes were found for all subjects and cell types, which can be explored at the interactive online portal (capblood-seq.caltech.edu, the content of which is incorporated herein by reference in its entirety). As one example, subject S1's monocytes have a consistent downregulation (p=$9.1 \times 10^{-7}$, two-sided student t-test) of LIPA, a gene that is implicated in Lysosomal Acid Lipase Deficiency (FIG. 3C). Given the low abundance of monocytes in blood samples, such findings would typically only be discovered from a targeted blood test or RNA sequencing of isolated monocytes, either of which would only be performed if the disease was already suspected; this showcases how automated discovery in heterogeneous cell populations can be leveraged for personalized, preventative care.

Figure 5A:
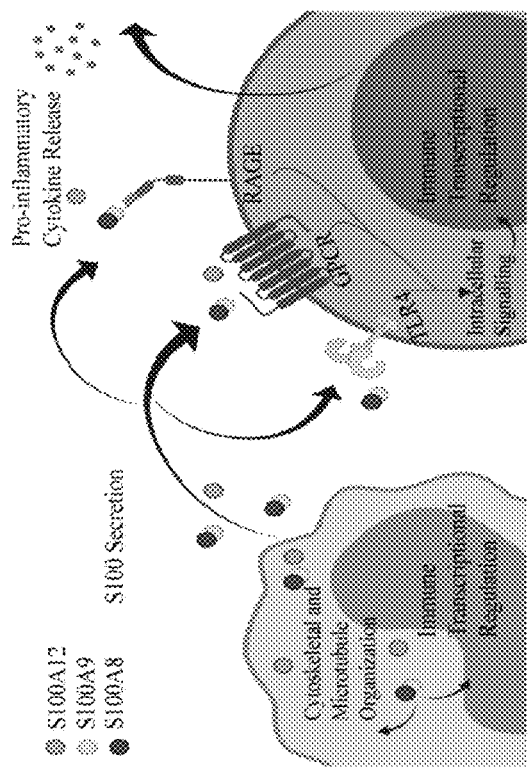
FIGS. 5A and 5B show that S100 pathway exhibits individual-specific regulation.
Figure 5B:
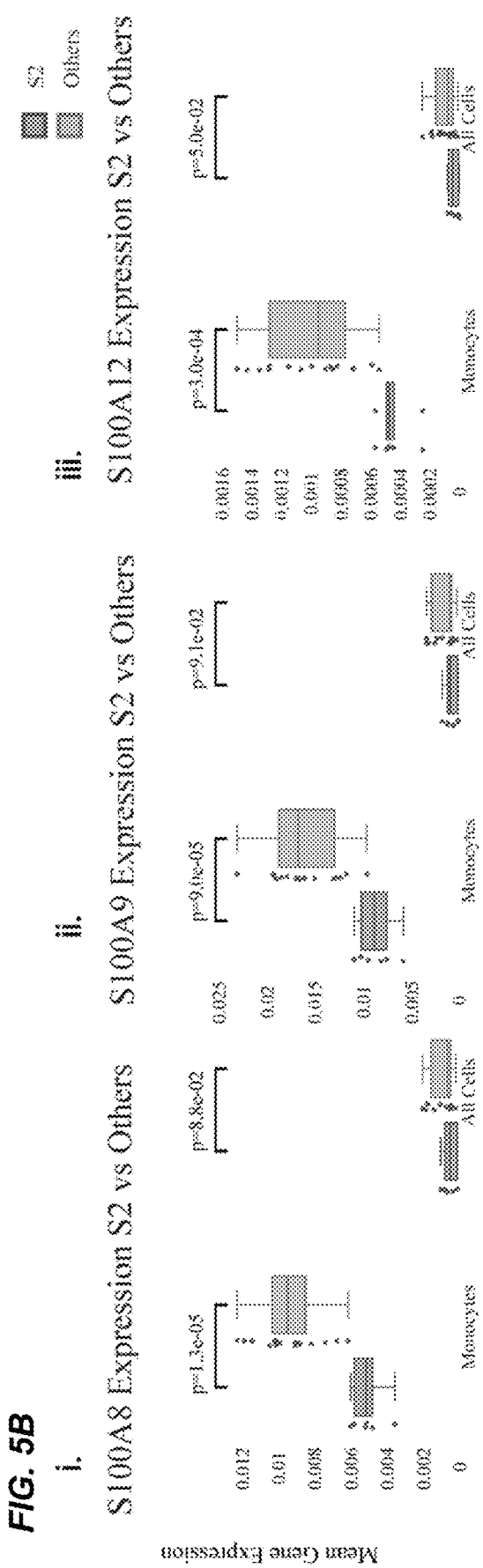
Figure 6:
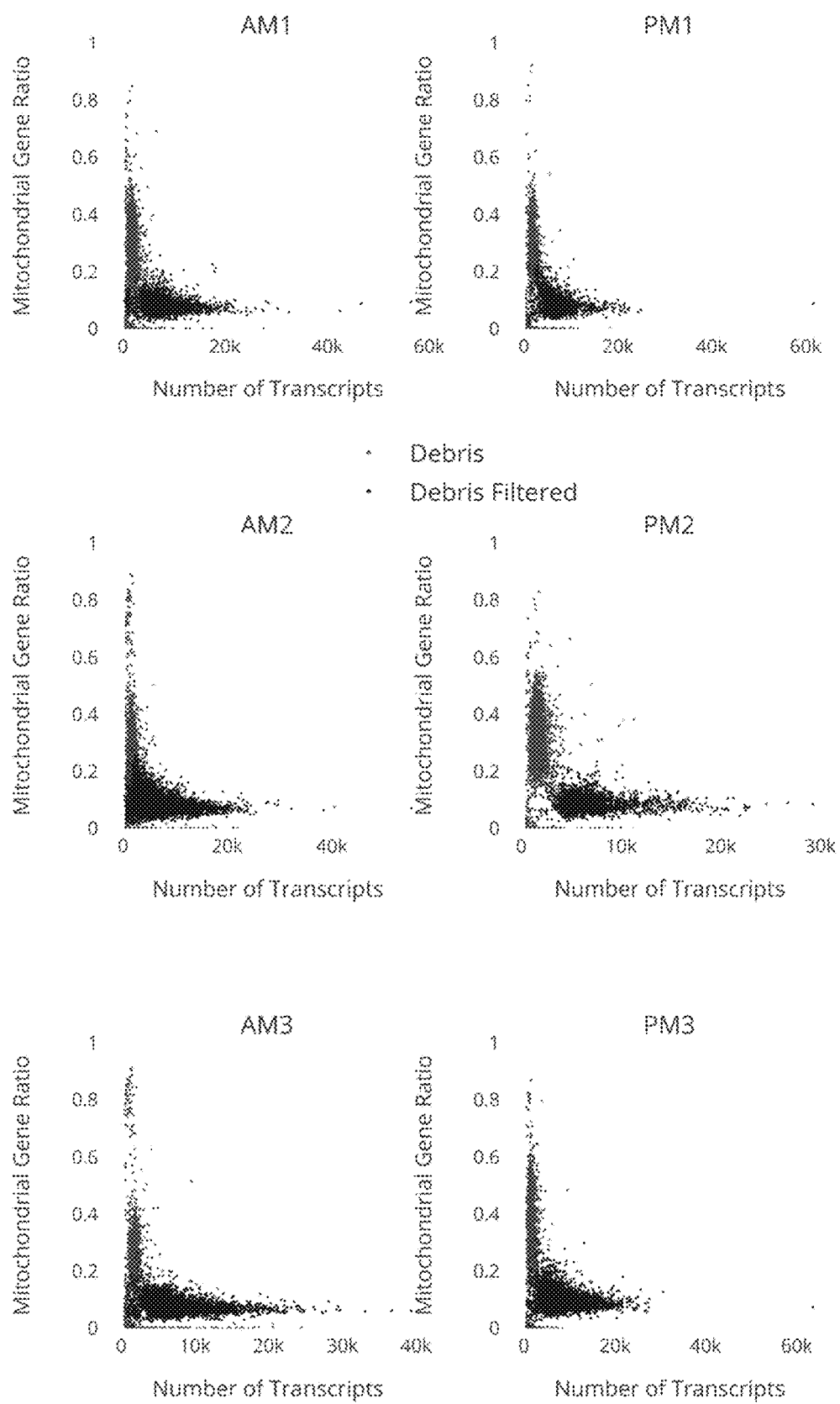
FIG. 6 shows characterization of debris removal pipeline across each time sample. Scatter plots of the total number of transcripts (UMIs) detected for each barcode (x-axis), and the ratio of transcripts that are mitochondrial (y-axis). These barcodes are the union of barcodes called by 10× Cellranger and our debris filtering pipeline. Barcodes colored red were flagged as debris and removed. The debris filtering pipeline appears to detect barcodes that have both a low transcript count, and a high mitochondrial gene ratio, or a rare number of cells that appear to have 0 mitochondrial genes. The counts of barcodes removed for each sample are in Table 6.
Figure 7:
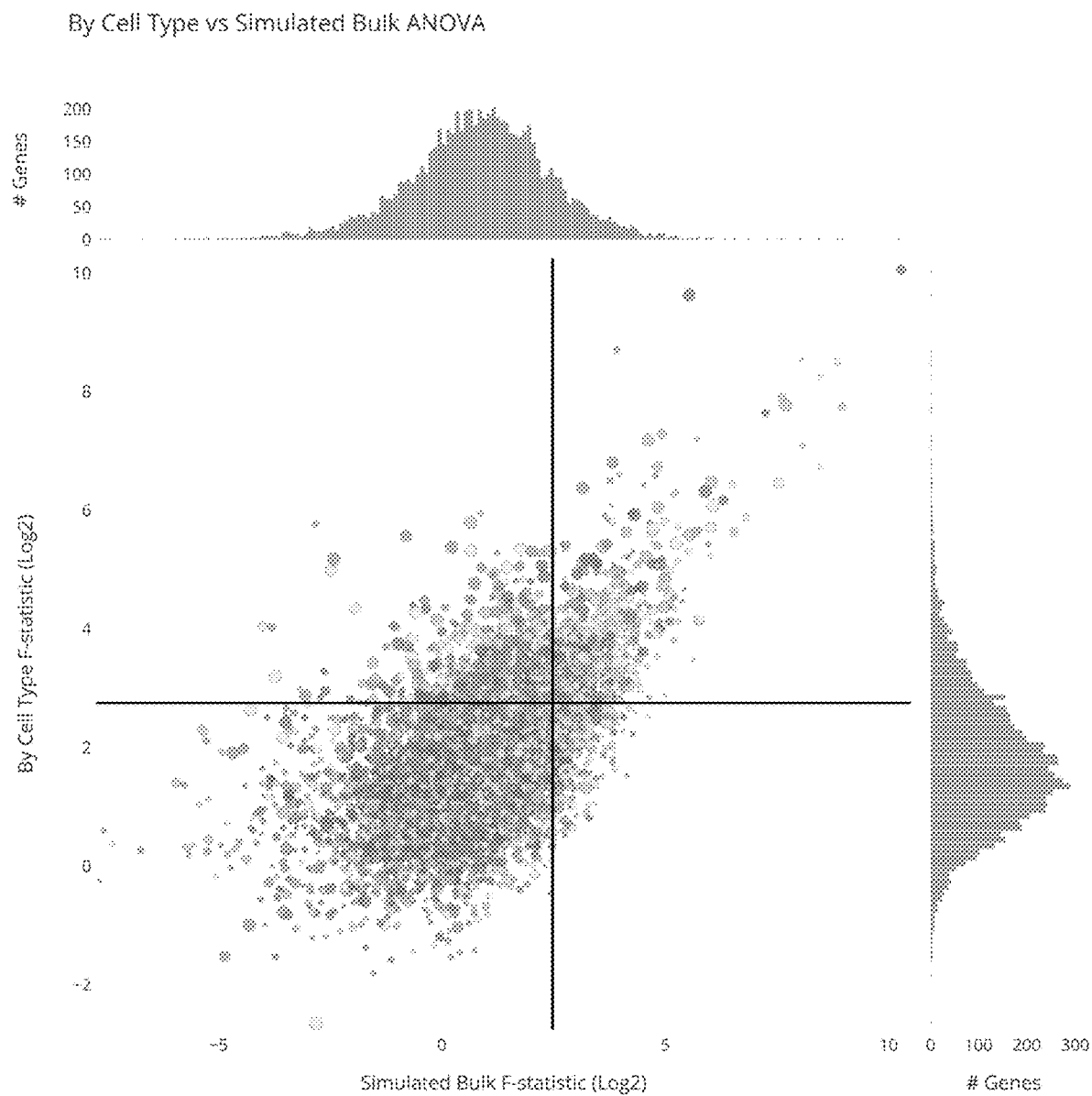
FIG. 7 shows comparison of individual specificity by cell type vs in simulated bulk data. Magnitude ($\log_2$ F statistic) of the variability in expression of genes between subjects, accounting for each cell type separately (y) and in simulated bulk (x). 1284/7034 (18.3%) of genes are above the subject specificity significance line (FDR<0.05, multiple comparison corrected) and are classified as subject-specific. Of these, only 637/1284 (49.6%) are also detected as subject-specific when simulating bulk RNA reads, despite the significantly lower multiple comparison correction burden (7034 tests as compared to 28,136 tests in the cell type case).
Figure 8A:
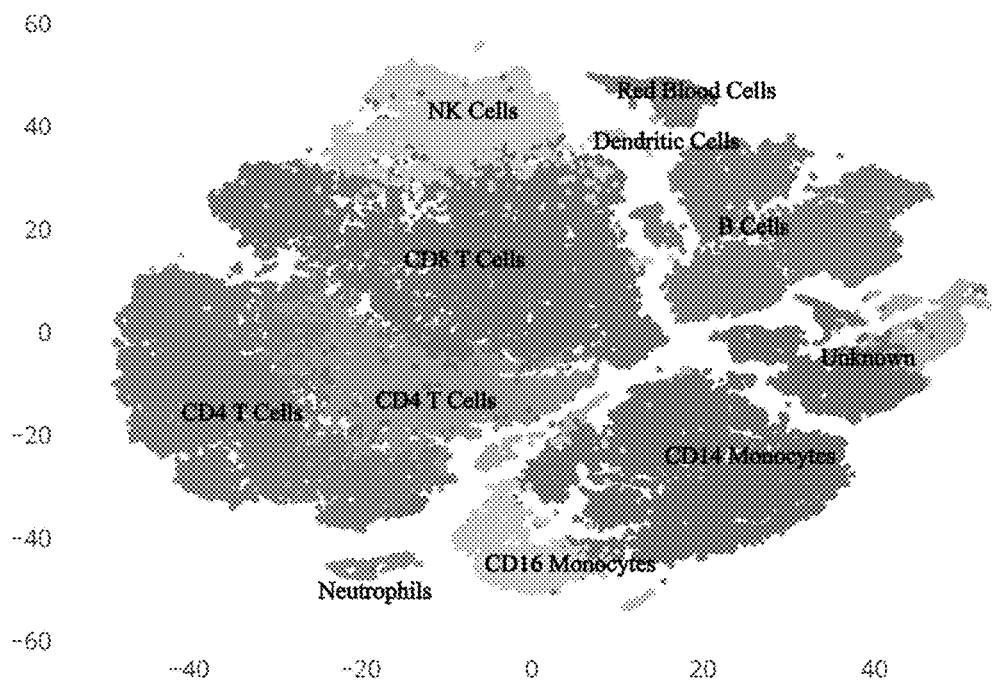
FIG. 8A-B show merged projections of capillary and venous blood cells. Capillary blood cells from this study (n=22) and venous blood cells from 3 other studies (n=11) were projected into a joint latent space using scVI.
Figure 8B:
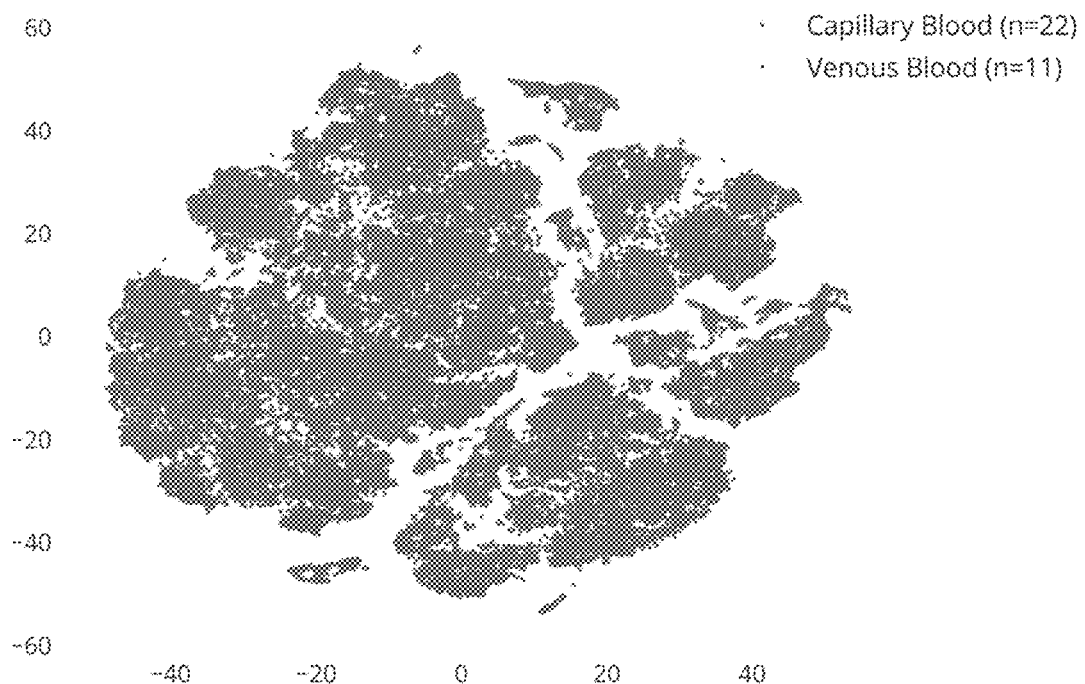
Figure 9:
FIG. 9 shows that immune cell type clusters detected in capillary blood. 2-dimensional t-SNE projection of the transcriptomes of all cells in all samples obtained from agglomerative clustering of latent gene expression. Cell clusters were annotated and grouped based on the markers presented in Table 2. Small unidentifiable clusters were are not included in the figure.

Immune function and disease pathways are enriched in subject-specific genes: Given that genes do not act alone, cell type-specific pathway differences were also found among subjects. In particular, Subject 2's S100A8, S100A9, and S100A12 genes, calcium-binding proteins that play an important role in macrophage inflammation, are significantly downregulated in monocytes (pS100A8=$1.3 \times 10^{-5}$, pS100A9=$9.0 \times 10^{-5}$, pS100A12=$3.0 \times 10^{-4}$, two-sided student t-test) compared to other subjects (FIGS. 5A and 5B). The findings were further explored by inspecting the pathways that are most enriched in individual and time-varying genes, and it was found that genes that are implicated in immune system function (p=0.085) and immune diseases (p=0.029) are more present in subject-specific genes (FIG. 3B). This stands in contrast to pathways of core cellular functions such as genetic information processing (p=0.029) and metabolism (p=0.095), which are less present in subject-specific genes.

Discussion

Genome and transcriptome sequencing projects have unveiled millions of genetic variants and associated gene expression traits in humans. However, large-scale studies of their functional effects performed through venous blood draws require tremendous effort to undertake, and this is exacerbated by the cost and complexity of single-cell transcriptome sequencing. Efforts such as the Immune Cell Census are underway to perform single-cell profiling of large cohorts, but their reliance on venous blood draws of PBMCs will likely limit the diversity and temporal resolution of their sample pool. The method, system and platform disclosed herein (including in this example) allows direct, scalable access to high resolution immune system transcriptome information of human subjects, lowering the barrier of entry for myriad new research avenues. Non-limiting examples of the applications that the methods, platforms and system disclosed herein can be used include: (1) tracking vulnerable populations over time, (2) Profiling individuals who are under home care to track disease progression and therapeutic response, such as transplant patients and people under quarantine, and (3) Tracking how stress, diet, and environmental conditions impact the immune system at short and long time scales, particularly in underrepresented populations who do not have easy access to hospitals or research institutions, such as people in rural or underdeveloped areas. Larger, more diverse subject pools coupled with time course studies of cell type gene expression in health and disease will have a dramatic impact on our ability to understand the baseline and variability of immune function.

Code Availability

Custom code made for diurnal and subject specific gene detection is available on github.com/thomsonlab/capbloodseq, the content of which is incorporated herein by reference in its entirety.

TABLE 1

Genes that ranked in top 20 that had pre-existing literature tying to circadian/diurnal expression

| Gene | DOI Reference (the content of each of which is incorporated herein by reference in its entirety) |
| --- | --- |
| DDIT4 | 10.7554/eLife.20214.001, 10.1073/pnas.1800314115 |
| SMAP2 | 10.1038/s41398-019-0671-7 |

TABLE 1-continued

Genes that ranked in top 20 that had pre-existing literature tying to circadian/diurnal expression

| Gene | DOI Reference (the content of each of which is incorporated herein by reference in its entirety) |
| --- | --- |
| RPL19 | 10.1128/MCB.00701-15 |
| RPS9 | 10.1073/pnas.1515308112 |
| PCPB1 | 10.1038/s41556-019-0441-z |
| RPS2 | 10.1073/pnas.1601895113 |
| COX5B | 10.1152/physiolgenomics.00066.2007 |

TABLE 2

Marker genes used to annotate clusters with specified cell population identity.

| Cells | Marker Genes |
| --- | --- |
| CD14 Monocytes | CD14, LYZ |
| CD16 Monocytes | FCGR3A, MS4A7 |
| CD4 T Cells | IL7R, CCR7 |
| CD8 T Cells | KLRG1, CD8A, CD8B |
| Natural Killer (NK) Cells | GNLY, KLRF1, KLRD1 |
| B Cells | BANK1, CD79A, CD79B, CD19 |

TABLE 3

Subject age and demographics. All subjects indicated to be healthy during the study.

| Subject | Age | Gender |
| --- | --- | --- |
| S1 | 32 | M |
| S2 | 41 | M |
| S3 | 34 | F |
| S4 | 26 | F |

TABLE 4

Details of studies used to get healthy venous blood single-cell RNA sequencing dataset for comparison with capillary blood.

| Subject | Age | Gender | Corresponding DOI (the content of each of which is incorporated herein by reference in its entirety) | Corresponding Study Identification |
| --- | --- | --- | --- | --- |
| S1 | 21 | M | doi.org/10.1038/s41598-020-59827-1 | Pre-THC-S1 |
| S2 | 21 | M | doi.org/10.1038/s41598-020-59827-1 | Pre-THC-S2 |
| S3 | 63 | F | doi.org/10.1126/sciimmunol.abd1554 | Sample 5_Normal 1 scRNA-seq [SW107] |
| S4 | 54 | F | doi.org/10.1126/sciimmunol.abd1554 | Sample 13_Normal 2 scRNA-seq [SW115] |
| S5 | 67 | F | doi.org/10.1126/sciimmunol.abd1554 | Sample 14_Normal 3 scRNA-seq [SW116] |
| S6 | 63 | M | doi.org/10.1126/sciimmunol.abd1554 | Sample 19_Normal 4 scRNA-seq [SW121] |
| S7 | 50 | M | doi.org/10.1073/pnas.1907883116 | CT1 |
| S8 | 70 | F | doi.org/10.1073/pnas.1907883116 | CT2 |
| S9 | 60 | F | doi.org/10.1073/pnas.1907883116 | CT3 |
| S10 | 70 | F | doi.org/10.1073/pnas.1907883116 | CT4 |
| S11 | 80 | M | doi.org/10.1073/pnas.1907883116 | CT5 |

TABLE 5

Number of genes in different cell types that is specific to each subject.

| | B Cells | Monocytes | NK Cells | T Cells | Any |
|---|---|---|---|---|---|
| S1 | 55 | 67 | 58 | 269 | 400 |
| S2 | 24 | 94 | 49 | 58 | 190 |
| S3 | 55 | 149 | 70 | 150 | 353 |
| S4 | 49 | 36 | 34 | 44 | 131 |

TABLE 6

Statistics for debris removal pipeline.

| | Cellranger Called | Removed | Added | Final # Cells | % Removed |
|---|---|---|---|---|---|
| AM1 | 5808 | 2662 | 21 | 3167 | 45.83 |
| PM1 | 3144 | 1302 | 12 | 1854 | 41.41 |
| AM2 | 8772 | 2037 | 20 | 6755 | 23.22 |
| PM2 | 6172 | 3587 | 0 | 2585 | 58.12 |
| AM3 | 6684 | 1408 | 10 | 5286 | 21.07 |
| PM3 | 7974 | 2370 | 4 | 5608 | 29.72 |

TABLE 7

Diurnally-varying genes (top 20 bolded).

| | | | | | | |
|---|---|---|---|---|---|---|
| DDIT4 | RPL36AL | ERGIC3 | KPNA6 | SESN1 | ISOC2 | TMEM258 |
| TYROBP | IFI16 | FLOT2 | ANXA5 | CHCHD10 | RNF125 | ESYT1 |
| COX5B | MT-ND4 | GIMAP6 | MIR142 | FBXO32 | FUOM | HDAC5 |
| NCR3 | RC3H1 | SH2D3C | TNRC6B | ZBTB16 | GZMK | PAXIP1-AS1 |
| RPS9 | RPL35A | TFEB | NFE2 | SRGAP2 | PIM1 | SNRPB |
| SNORA76 | RPL6 | HAPLN3 | CEBPD | GABARAP | MDH2 | KLF6 |
| MT-ND3 | TMEM106A | MT-ND5 | NKG7 | ZFP36 | CD44 | PPP1R18 |
| PCBP1 | RPS18 | AKNA | PLBD1 | HSP90AB1 | ADRB2 | TKT |
| RPS2 | SERPINB1 | SEC16A | RPL5 | ITGA4 | ATP8B2 | LYPLA1 |
| ABCA2 | FMNL1 | CYTH4 | ST3GAL5 | MAN2B2 | BSG | MGEA5 |
| CBFA2T2 | MT-ND1 | IRF4 | AKAP13 | TP53 | KIAA0020 | CHMP1B |
| RPL19 | SEC61B | MORF4L1 | EEF1B2 | CASP2 | CTSH | FAM105A |
| CDC42SE2 | SF1 | TRIP11 | DNPH1 | BRI3 | PABPC1 | GPR82 |
| LMO2 | FKBP5 | S1PR1 | CTSA | C19orf10 | RPL8 | BCL3 |
| RPS8 | HBB | SSNA1 | CYSTM1 | CRELD2 | SEC22C | AIDA |
| CELF2 | KLF4 | COX4I1 | CELF1 | RRAGC | PSD4 | NBEAL2 |
| EIF4A2 | MBD6 | MYD88 | TSPO | GNB2L1 | SPG21 | NDUFB8_1 |
| GPR65 | MRPL52 | ANKRD49 | HIVEP2 | HELZ2 | C3AR1 | RPL14 |
| RPS15 | PPIB | GPATCH4 | DBP | GZMH | DNAJC13 | RPS23 |
| SMAP2 | SAMD4B | OGDH | EIF4B | TRANK1 | SELL | PRELID1 |
| MAT2B | RPL32 | PPM1K | ARF6 | SLFN11 | SMC1A | SH3BP5 |
| RPL11 | USP15 | TOR3A | TBL1X | GAPDH | ADIPOR1 | WDFY2 |
| RSL1D1 | RENBP | ZDHHC2 | TMBIM6 | OSBPL10 | ARL1 | ARHGDIA |
| FPR1 | C16orf54 | RPS24 | VPS28 | PIK3CD | C16orf74 | F8A1 |
| LINC00649 | CALR | NCOA2 | LINC00324 | PSMA7 | NMD3 | C3orf62 |
| RBM3 | CBX7 | POU2F2 | MOB3A | ZMIZ1 | RASSF3 | GSTP1 |
| RPL13 | CDIP1 | MAP2K1 | DAZAP2 | CCND3 | TCEAL8 | AC092580.4 |
| SREK1IP1 | INPPL1 | AHNAK | DPH3 | TIMP1 | FASLG | ORAI2 |
| HSPA5 | RPL39 | SLA | GBP4 | NLRC5 | ASGR1 | HDAC9 |
| RPS14 | RSPH3 | CLDND1 | PRMT1 | P2RX5 | NPDC1 | MLLT6 |
| SLC25A6 | SGPP1 | HDAC10 | CAT | RPS13 | UBA1 | DNM2 |
| TXNIP | ITGB2 | RPL28 | CYB561 | TNRC18 | CHD7 | OXNAD1 |
| RPL7A | PTBP1 | SELPLG | PAFAH1B2 | RPL3 | GAA | BCL6 |
| LIMD1 | TGFBR2 | ZCCHC17 | SH3BP1 | RPL29 | IGSF6 | CD99 |
| MPEG1 | ZC2HC1A | NEAT1 | WDR60 | RPS6KA3 | MSMO1 | TSPAN4 |
| CD55 | TCF7 | SPON2 | YTHDC2 | BATF | RHOC | VAV3 |
| LSP1_1 | TRAPPC6A | MYL6 | ZNF429 | DGKE | S100A4 | CLPP |
| STK10 | TMC8 | NOL12 | HOTAIRM1 | NCAPD3 | S100PBP | A2M-AS1 |
| CX3CR1 | FLNA | RPL18 | TLR7 | UPF3B | FAM198B | AIMP1 |
| PCBP2 | C9orf142 | SAP30 | ARHGAP17 | VPS39 | TUBA4A | ATP5G2 |
| VIM-AS1 | CYSLTR1 | TFAM | PANK3 | SSR4 | TMED10 | CCNDBP1 |
| CTDSP2 | C19orf53 | TSC22D3 | RAB1B | BCL2 | POLR2L | CHPT1 |
| GNAS | SERF2 | TUBA1A | ARPC1B | CBX6 | RALGDS | DUSP2 |
| CORO7 | HADHA | CALM1 | EZR | PSMB6 | P4HB | DZIP3 |
| HIGD2A | SUN2 | EIF3K | LRRC8D | FUCA1 | MBNL1 | FKBP1A |
| MT-ND2 | PPP2R1A | TCEB2 | WIPF2 | DIP2B | PEA15 | KLRK1 |
| NDUFB9 | CYTIP | FAU | S100A9 | RAB7L1 | PSMD10 | NEK7 |
| RNFT1 | PNRC1 | C19orf24 | STIM2 | BLCAP | RPL10A | P2RX1 |
| CD180 | TAF1D | PRDM1 | HNRNPC | C15orf40 | SASH3 | SLC35A3 |
| CRIP1_1 | S100A6 | CXCR3 | LINC01116 | CSK | LYRM7 | IFNG-AS1 |
| PDIA3 | RPS25 | STAG3 | LMO4 | MSRB1 | PA2G4 | TMEM2 |
| MAU2 | PIEZO1 | HCST | UBALD2 | NCF2 | RPS16 | ACSL6 |
| ISG20 | RAB18 | FDX1 | HCFC1 | RPS7 | SRSF7 | LGALS1 |
| BTG1 | IL2RB | MT-CO1 | MXD4 | SMAD5 | GNB1 | |
| CXCR4 | ALCAM | CTSW | SYTL3 | DHRS7 | NFATC3 | |
| GZMM | DENND4B | ATP5I | NDUFA3 | MANF | DCP2 | |
| IGLL5 | AP2M1 | AGPAT1 | TCEB3 | TPP1 | GNAI2 | |

TABLE 8

The 119 genes out of the above 395 that were detected at the population level.

| | | | | | | |
|---|---|---|---|---|---|---|
| DDIT4 | STK10 | FMNL1 | AP2M1 | EIF3K | SYTL3 | KIAA0020 |
| SNORA76 | PCBP2 | FKBP5 | FLOT2 | MT-CO1 | NDUFA3 | ARL1 |
| MT-ND3 | CTDSP2 | MRPL52 | SH2D3C | ATP5I | FBXO32 | UBA1 |
| PCBP1 | CORO7 | PPIB | MORF4L1 | AGPAT1 | GABARAP | S100PBP |
| RPS2 | HIGD2A | SAMD4B | S1PR1 | MIR142 | TP53 | TUBA4A |
| ABCA2 | MT-ND2 | USP15 | COX4I1 | ST3GAL5 | CASP2 | PSMD10 |
| CBFA2T2 | NDUFB9 | C16orf54 | ANKRD49 | DBP | HELZ2 | SASH3 |
| RPS8 | RNFT1 | CALR | GPATCH4 | ARF6 | OSBPL10 | PA2G4 |
| EIF4A2 | CD180 | CBX7 | ZDHHC2 | MOB3A | PIK3CD | RPS16 |
| GPR65 | CRIP1_1 | INPPL1 | RPS24 | CYB561 | CCND3 | NFATC3 |
| SMAP2 | PDIA3 | RPL39 | MAP2K1 | PAFAH1B2 | NLRC5 | HDAC5 |
| MAT2B | MAU2 | TRAPPC6A | SLA | SH3BP1 | PSMB6 | GPR82 |
| RSL1D1 | ISG20 | C19orf53 | CLDND1 | ARHGAP17 | BLCAP | RPL14 |
| RBM3 | BTG1 | PPP2R1A | HDAC10 | HNRNPC | CSK | ORAI2 |
| HSPA5 | MT-ND4 | CYTIP | RPL28 | LINC01116 | SMAD5 | OXNAD1 |
| RPS14 | RPL6 | PNRC1 | TFAM | LMO4 | MANF | CHPT1 |
| TXNIP | TMEM106A | TAF1D | TSC22D3 | HCFC1 | MDH2 | SLC35A3 |

TABLE 9

The 276 out of the 395 genes that were unique to cell subtype populations.

| | | | | | | |
|---|---|---|---|---|---|---|
| TYROBP | CDIP1 | SELPLG | DAZAP2 | TIMP1 | DNAJC13 | FAM105A |
| COX5B | RSPH3 | ZCCHC17 | DPH3 | P2RX5 | SELL | BCL3 |
| NCR3 | SGPP1 | NEAT1 | GBP4 | RPS13 | SMC1A | AIDA |
| RPS9 | ITGB2 | SPON2 | PRMT1 | TNRC18 | ADIPOR1 | NBEAL2 |
| RPL19 | PTBP1 | MYL6 | CAT | RPL3 | C16orf74 | NDUFB8_1 |
| CDC42SE2 | TGFBR2 | NOL12 | WDR60 | RPL29 | NMD3 | RPS23 |
| LMO2 | ZC2HC1A | RPL18 | YTHDC2 | RPS6KA3 | RASSF3 | PRELID1 |
| CELF2 | TCF7 | SAP30 | ZNF429 | BATF | TCEAL8 | SH3BP5 |
| RPS15 | TMC8 | TUBA1A | HOTAIRM1 | DGKE | FASLG | WDFY2 |
| RPL11 | FLNA | CALM1 | TLR7 | NCAPD3 | ASGR1 | ARHGDIA |
| FPR1 | C9orf142 | TCEB2 | PANK3 | UPF3B | NPDC1 | F8A1 |
| LINC00649 | CYSLTR1 | FAU | RAB1B | VPS39 | CHD7 | C3orf62 |
| RPL13 | SERF2 | C19orf24 | ARPC1B | SSR4 | GAA | GSTP1 |
| SREK1IP1 | HADHA | PRDM1 | EZR | BCL2 | IGSF6 | AC092580.4 |
| SLC25A6 | SUN2 | CXCR3 | LRRC8D | CBX6 | MSMO1 | HDAC9 |
| RPL7A | S100A6 | STAG3 | WIPF2 | FUCA1 | RHOC | MLLT6 |
| LIMD1 | RPS25 | HCST | S100A9 | DIP2B | S100A4 | DNM2 |
| MPEG1 | PIEZO1 | FDX1 | STIM2 | RAB7L1 | FAM198B | BCL6 |
| CD55 | RAB18 | CTSW | UBALD2 | C15orf40 | TMED10 | CD99 |
| LSP1_1 | IL2RB | KPNA6 | MXD4 | MSRB1 | POLR2L | TSPAN4 |
| CX3CR1 | ALCAM | ANXA5 | TCEB3 | NCF2 | RALGDS | VAV3 |
| VIM-AS1 | DENND4B | TNRC6B | SESN1 | RPS7 | P4HB | CLPP |
| GNAS | ERGIC3 | NFE2 | CHCHD10 | DHRS7 | MBNL1 | A2M-AS1 |
| CXCR4 | GIMAP6 | CEBPD | ZBTB16 | TPP1 | PEA15 | AIMP1 |
| GZMM | TFEB | NKG7 | SRGAP2 | ISOC2 | RPL10A | ATP5G2 |
| IGLL5 | HAPLN3 | PLBD1 | ZFP36 | RNF125 | LYRM7 | CCNDBP1 |
| RPL36AL | MT-ND5 | RPL5 | HSP90AB1 | FUOM | SRSF7 | DUSP2 |
| IFI16 | AKNA | AKAP13 | ITGA4 | GZMK | GNB1 | DZIP3 |
| RC3H1 | SEC16A | EEF1B2 | MAN2B2 | PIM1 | DCP2 | FKBP1A |
| RPL35A | CYTH4 | DNPH1 | BRI3 | CD44 | GNAI2 | KLRK1 |
| RPS18 | IRF4 | CTSA | C19orf10 | ADRB2 | TMEM258 | NEK7 |
| SERPINB1 | TRIP11 | CYSTM1 | CRELD2 | ATP8B2 | ESYT1 | P2RX1 |
| MT-ND1 | SSNA1 | CELF1 | RRAGC | BSG | PAXIP1-AS1 | IFNG-AS1 |
| SEC61B | MYD88 | TSPO | GNB2L1 | CTSH | SNRPB | TMEM2 |
| SF1 | OGDH | HIVEP2 | GZMH | PABPC1 | KLF6 | ACSL6 |
| HBB | PPM1K | EIF4B | TRANK1 | RPL8 | PPP1R18 | LGALS1 |
| KLF4 | TOR3A | TBL1X | SLFN11 | SEC22C | TKT | |
| MBD6 | NCOA2 | TMBIM6 | GAPDH | PSD4 | LYPLA1 | |
| RPL32 | POU2F2 | VPS28 | PSMA7 | SPG21 | MGEA5 | |
| RENBP | AHNAK | LINC00324 | ZMIZ1 | C3AR1 | CHMP1B | |

TABLE 10

The 219 of the 395 genes that are druggable.

| | | | | | | |
|---|---|---|---|---|---|---|
| TYROBP | IFI16 | HAPLN3 | NFE2 | ITGA4 | ADRB2 | CHMP1B |
| COX5B | MT-ND4 | MT-ND5 | CEBPD | MAN2B2 | ATP8B2 | GPR82 |
| NCR3 | RC3H1 | AKNA | PLBD1 | TP53 | BSG | BCL3 |
| MT-ND3 | SERPINB1 | SEC16A | RPL5 | CASP2 | CTSH | PRELID1 |
| PCBP1 | MT-ND1 | IRF4 | ST3GAL5 | CRELD2 | C3AR1 | WDFY2 |
| ABCA2 | SF1 | TRIP11 | AKAP13 | GNB2L1 | SELL | GSTP1 |

TABLE 10-continued

The 219 of the 395 genes that are druggable.

| | | | | | | | |
|---|---|---|---|---|---|---|---|
| CBFA2T2 | FKBP5 | S1PR1 | DNPH1 | HELZ2 | SMC1A | ORAI2 | |
| LMO2 | HBB | COX4I1 | CTSA | GZMH | ADIPOR1 | HDAC9 | |
| EIF4A2 | KLF4 | MYD88 | CELF1 | GAPDH | FASLG | MLLT6 | |
| GPR65 | PPIB | PPM1K | TSPO | OSBPL10 | ASGR1 | DNM2 | |
| RPS15 | USP15 | NCOA2 | HIVEP2 | PIK3CD | UBA1 | OXNAD1 | |
| MAT2B | RENBP | POU2F2 | DBP | PSMA7 | CHD7 | BCL6 | |
| FPR1 | CALR | MAP2K1 | TBL1X | ZMIZ1 | GAA | CD99 | |
| HSPA5 | INPPL1 | CLDND1 | MOB3A | CCND3 | MSMO1 | VAV3 | |
| SLC25A6 | RSPH3 | HDAC10 | PRMT1 | TIMP1 | TUBA4A | CLPP | |
| TXNIP | SGPP1 | SELPLG | CAT | P2RX5 | TMED10 | AIMP1 | |
| RPL7A | ITGB2 | SPON2 | PAFAH1B2 | RPS6KA3 | RALGDS | CCNDBP1 | |
| LIMD1 | PTBP1 | TFAM | SH3BP1 | BATF | P4HB | DUSP2 | |
| CD55 | TGFBR2 | TUBA1A | TLR7 | DGKE | MBNL1 | DZIP3 | |
| STK10 | TCF7 | CALM1 | PANK3 | BCL2 | PEA15 | FKBP1A | |
| CX3CR1 | TMC8 | TCEB2 | ARPC1B | PSMB6 | PSMD10 | KLRK1 | |
| CTDSP2 | FLNA | PRDM1 | EZR | FUCA1 | LYRM7 | NEK7 | |
| GNAS | CYSLTR1 | CXCR3 | LRRC8D | CSK | PA2G4 | P2RX1 | |
| HIGD2A | HADHA | STAG3 | S100A9 | MSRB1 | GNB1 | SLC35A3 | |
| MT-ND2 | PPP2R1A | HCST | STIM2 | SMAD5 | NFATC3 | TMEM2 | |
| NDUFB9 | PNRC1 | FDX1 | LMO4 | DHRS7 | TMEM258 | ACSL6 | |
| CD180 | TAF1D | MT-CO1 | NDUFA3 | MANF | HDAC5 | LGALS1 | |
| PDIA3 | PIEZO1 | CTSW | TCEB3 | TPP1 | KLF6 | | |
| BTG1 | IL2RB | ATP5I | SESN1 | RNF125 | PPP1R18 | | |
| CXCR4 | ALCAM | AGPAT1 | ZBTB16 | GZMK | TKT | | |
| GZMM | AP2M1 | KPNA6 | ZFP36 | PIM1 | LYPLA1 | | |
| IGLL5 | TFEB | ANXA5 | HSP90AB1 | CD44 | MGEA5 | | |

TABLE 11

The 1284 individually-varying genes.

| | | | | | | | |
|---|---|---|---|---|---|---|---|
| RPS4Y1 | EBPL | LGALS3BP | ALKBH7 | MYBL1 | GK5 | CD44 | |
| HLA-DRB1 | THBS1 | CD247 | CLEC4D | PTPRE | CDK12 | TMC6 | |
| RETN | RPS9 | H1FX | HIGD2A | ITGAX | VAPA | DYNLRB1 | |
| SCGB3A1 | CROCCP2 | GPX4 | CX3CR1 | DTHD1 | LONP2 | A1BG | |
| EIF1AY | CAPN12 | KIAA0040 | TNFRSF18 | LINC00998 | CANX | FAM104A | |
| DDX3Y | SMARCA2 | TNFRSF1B | VPS16 | ALPK1 | IRF7 | SLC20A1 | |
| MZT2A | MARCO | GIMAP2 | ZNF22 | IL2RG | MYO1E | CD9 | |
| RPS26 | DAZAP2 | LPIN1 | PTGIR | S100A9 | GBP5 | NIPSNAP3A | |
| XIST | SKAP2 | TCF7 | PPM1F | AKAP17A | SF1 | VTI1B | |
| HLA-DQA2 | RCBTB2 | CXXC5 | IRF8 | SH3KBP1 | DDRGK1 | B4GALT1 | |
| MYOM2 | ITM2A | ZNF259 | TTC39B | GCNT1 | H2AFZ | GCC2 | |
| RP11-81H14.2 | SULF2 | MAN1A1 | FAIM3 | ARPC5 | GRAMD1A | TMEM123 | |
| GNLY | NCF1 | AKR1C3 | RPLP2 | MRPL54 | CD97 | ABHD17A | |
| KANSL1-AS1 | CHURC1 | SLC38A1 | NFKB1 | CAPN2 | RPS8 | FAM46C | |
| LTA4H | GBP3 | TYW3 | GOLGA8A | CISD1 | TRIM28 | RPS20 | |
| PRMT2 | ATHL1 | SLFN5 | ARID5B | ARHGAP9 | AP3B1 | USP10 | |
| CCZ1B | NDUFS5 | TSPAN2 | HNRNPU | ITM2B | STT3B | G3BP1 | |
| CHI3L2 | SCN3A | SAR1A | TMEM66 | YEATS4 | NAP1L1 | DAB2 | |
| CD151 | ATP6V1G1 | SOD2 | JDP2 | GALNT10 | SAP30 | PLXND1 | |
| LILRA3 | CENPK | HLA-DPA1 | CD74 | ZNF609 | SCP2 | RPS3 | |
| CHCHD2 | SYNGR1 | EFHD2 | SSBP4 | ARCN1 | PLEKHJ1 | ABI3 | |
| EIF1AX | BCL7C | FKBP11 | CCR6 | RP1-3J17.3 | ATP6V1E1 | RNF144B | |
| TIMM10 | YWHAQ | SPATS2L | GZMA | TNFRSF25 | PCMTD2 | CSNK1A1 | |
| SIGLEC14 | LTBP3 | LYSMD2 | BIRC3 | LST1 | ECHDC1 | WHAMM | |
| FCER1G | STXBP2 | MATK | PWP1 | KDM5C | SUPT4H1 | IVNS1ABP | |
| RPS4X | EIF4E3 | VDAC1 | ZSCAN18 | APC | PLAC8 | RAP2A | |
| DIP2A | MERTK | ATP5G1 | M6PR | COA6 | PPIL3 | CDC25B | |
| SNHG8 | AP1S2 | SH2B2 | BACE2 | PTTG1 | CIB1 | MTPN | |
| HLA-C | RPL28 | DDX60L | ITGAM | COL6A2 | LCP1 | EIF3E | |
| AK5 | CD55 | GNG2 | PPAPDC1B | DTD1 | SPTBN1 | TMEM50A | |
| FCGR3A | CFD | HES4 | EEF2 | GSTP1 | SUB1 | PPM1M | |
| DAPK1 | EBP | FCRLA | PLEKHA2 | NPC1 | CBLB | AKR1A1 | |
| CNN2 | PDE4D | COPRS | RNF130 | NDUFB10 | MPC1 | PRR5L | |
| RPS10 | CD3G | RPS12 | KCNE3 | CFLAR | VMP1 | LTB | |
| FOLR3 | APEX1 | EIF6 | IFITM2 | ASF1A | KIAA1033 | CD86 | |
| CCZ1 | TRAT1 | MT-ND5 | MYL12B | TSPAN4 | METTL15 | METRNL | |
| VSTM1 | NOP10 | SNRPD2 | POLR2L | GABARAPL1 | CD8B | UBXN7 | |
| PPA1 | LILRB1 | PDGFD | LINC00152 | BRD4 | COPE | RGCC | |
| CHPT1 | RABAC1 | PARP14 | ESYT2 | CHN2 | PCBD1 | LMAN2 | |
| CD52 | LGALS9B | BEX3 | KIAA0355 | RPL5 | RSAD2 | RAB9A | |
| CBWD2 | CEP78 | MFHAS1 | ADK | CD40LG | VAMP4 | FKBP5 | |
| TTC39C | KCNAB2 | MGLL | LRRN3 | EZR | PRR5 | XRCC4 | |
| CCDC167 | NPDC1 | GZMB | GDI2 | DNAJB9 | CCND3 | MANBA | |
| SMDT1 | MX1 | PADI4 | SMIM20 | CD164 | IL6R | MIDN | |

TABLE 11-continued

The 1284 individually-varying genes.

| | | | | | | | |
|---|---|---|---|---|---|---|---|
| RPL36AL | S1PR5 | IGFBP7 | LY86 | RAN | SLC43A2 | MAP3K5 | |
| RIC3 | CBWD1 | AGTRAP | NBPF12 | STX11 | DUSP2 | TRA2B | |
| CCL5 | NABP1 | FAM129A | PPP2R5C | SLFN12L | MGA | NPAT | |
| MT2A | SH3BGRL3 | DNAJC15 | PRKCA | CA5B | FAM3C | TTC9 | |
| EIF5A | FLNA | IGJ | CD93 | CHMP4B | DENND2D | COX5B | |
| NAPRT1 | TNFSF14 | S100A8 | RNASE2 | TPTEP1 | TRAPPC2 | CDR2 | |
| MT-CYB | PLXNC1 | C12orf57 | OSGEP | BTF3L4 | HIVEP3 | SLC25A28 | |
| CLEC12A | ARPC1B | PSME2 | PPIB | SYTL3 | RP11-25K19.1 | MAPRE1 | |
| NSG1 | DDT | NCR1 | ZNF439 | METTL9 | SNX9 | FOXO1 | |
| RPL27A | SNAPC5 | PARP8 | SRA1 | TMEM173 | SAMSN1 | OST4 | |
| LITAF | NPIPB5 | GLRX | CLEC7A | RCAN3 | TIMP1 | POM121 | |
| LAIR2 | GYPC | FAR1 | BCAS4 | 44261 | MYL6 | EMP3 | |
| MXRA7 | CCL4 | C3AR1 | CACUL1 | AC006129.2 | HSPA6 | LYN | |
| FRG1B | IL7R | HLA-DPB1 | SFT2D2 | PLOD1 | LIMD1 | BTK | |
| LIPA | RRP7A | MFSD10 | ZYX | PLD4 | ANKRD26 | CD5 | |
| BIN1 | CPNE1 | RPH3A | HENMT1 | B4GALT4 | APOBR | C11orf21 | |
| HLA-E | IFI44 | CD99 | PLXDC2 | CASP10 | FLNB | SNTB2 | |
| LYZ | ID2 | BPGM | GRK6 | ACSL6 | LRRC8C | IMP4 | |
| EMR1 | KLRG1 | RGS10 | NCK2 | OS9 | IL10RA | REL | |
| HLA-DRA | IFI6 | PNRC1 | CHD7 | RBM43 | RPS27A | KCTD20 | |
| TNFSF13B | TMEM18 | FURIN | PDXDC1 | NUP88 | ITGA6 | CAMK2D | |
| MYL12A | XRRA1 | SNRNP27 | HK2 | 44256 | MRFAP1 | FAM126A | |
| SUMF2 | NRG1 | KIAA0930 | HN1 | RP11-660L16.2 | SESN3 | GFPT1 | |
| PPT1 | NGFRAP1 | TMEM14B | KDM4B | NUMB | NUTM2A-AS1 | VASP | |
| ARL17A | ORMDL3 | PTEN | RP11-343N15.5 | MT-CO3 | RPL15 | C7orf55 | |
| CD300C | NELL2 | ANK3 | TNNI2 | TXNIP | F5 | CBX6 | |
| FIBP | ANXA4 | BMP2K | SPCS2 | TXLNG | MID1IP1 | TKT | |
| GTF2H2 | PPIA | F13A1 | C16orf74 | GPR114 | MAP3K7CL | JAZF1 | |
| ARHGAP24 | S100A10 | COMTD1 | CAST | ZFX | IDH3G | SOS1 | |
| BEX2 | ISG15 | CEPT1 | C14orf1 | EIF2AK2 | AKAP7 | CCM2 | |
| AC079767.4 | TTC38 | RILPL2 | CD63 | RASSF2 | HOOK2 | LAMTOR2 | |
| IL32 | FABP5 | GMPR2 | SERPINB1 | RPL24 | FAM102A | HMGN3 | |
| GTPBP6 | RTKN2 | IFI27L2 | DBI | SNX10 | ODF2L | HCLS1 | |
| VIM | DSE | ELP5 | ABHD2 | CD72 | MSRB1 | PBXIP1 | |
| RPS7 | GIMAP1 | SYAP1 | OSBPL8 | AOAH | PIN4 | DCTN3 | |
| ZRSR2 | MT-ND3 | JPX | RHOA | ZEB2 | SLAMF6 | TMEM55A | |
| HLA-A | CCDC109B | CLK1 | TNNT1 | SNCA | SORL1 | COMMD10 | |
| SERPINB6 | RPL12 | FAM134B | RHOQ | RPS24 | CTSS | IGFLR1 | |
| EIF2S3 | HEBP1 | PLP2 | MARCKSL1 | FADS1 | ATP11B | CAPG | |
| LINC00649 | DSTN | RASA4 | ATP5G2 | YWHAB | ZNF274 | C15orf57 | |
| HLA-B | TSPO | SH3TC1 | AKAP10 | SAMHD1 | RAB37 | C1orf21 | |
| HLA-DQB1 | CTD-2006K23.1 | SAMD9L | CNIH4 | EIF3G | RPL21 | ATM | |
| USP53 | CLIC1 | CD37 | C16orf87 | RECQL | FAM214B | ABRACL | |
| RASAL3 | BST1 | GPR56 | KLRC2 | MDM2 | SOX4 | TNFAIP3 | |
| CSTB | SH3BP5 | ASAP1 | BLOC1S1 | RINL | ZNF626 | KLRB1 | |
| TMEM8A | LINC00969 | NDUFA3 | ACTR2 | SDF2L1 | GRINA | TNFSF12 | |
| SULT1A1 | MACROD2 | SH2D2A | RAP1B | MBOAT1 | RAP2B | ZNF787 | |
| LGALS1 | CD48 | KIAA1598 | GFOD1 | GUK1 | FN3KRP | FDFT1 | |
| C8orf59 | SIRPB1 | WARS | JUP | SRSF5 | CLDND1 | HEXDC | |
| LDLR | PPP2R5A | IRAK3 | VNN2 | EIF4G2 | LOH12CR1 | TGFBR3 | |
| AL592183.1 | FASLG | RPL8 | VNN3 | CTSA | SNORD3A | SMCO4 | |
| NAAA | ARL6IP5 | FAM195A | UBQLN2 | MS4A7 | ARL14EP | SLC4A7 | |
| THEMIS2 | RPL10A | ARL4C | GNPTAB | UBE2R2 | PDCD6 | OSTF1 | |
| KCNMA1 | TMSB10 | RGS3 | LPCAT2 | RP11-1398P2.1 | MRPS14 | RAB7L1 | |
| MT-ATP6 | GLCCI1 | EVI2B | CHMP3 | PABPC1 | CYP27A1 | TRIM44 | |
| PSMD5-AS1 | CDA | CYTIP | FUT7 | ZNF814 | CAMK1 | FOXN2 | |
| GIMAP4 | TYROBP | GNB4 | ANPEP | IL2RB | STK32C | TXNRD1 | |
| APOBEC3A | PSMB9 | PTPN22 | ANXA5 | SOD1 | EIF3F | ASCL2 | |
| PSTPIP2 | S100A12 | CD200 | PTPN6 | SPG20 | RPL7A | ZBTB38 | |
| CD3E | MRPL41 | PTGER2 | SELL | PAWR | DDOST | JMJD1C | |
| HOPX | SFT2D1 | MDH2 | RNF157 | HOMER3 | TMEM167A | ITGB1BP1 | |
| LGALS2 | PLA2G16 | TUFM | LL22NC03-2H8.5 | ADRB2 | SRP54 | BACH2 | |
| RPS13 | ALOX5AP | C1orf228 | NDUFB7 | XAF1 | IAKMIP2 | CHMP4A | |
| GZMH | PLIN2 | C19orf59 | IL6ST | ISCU | CCR2 | FOXP1 | |
| LINC00667 | TOMM7 | N4BP2 | PYCR2 | COMMD6 | S100A11 | IQGAP1 | |
| EPB41L3 | SYTL2 | RPLP1 | POLM | HNMT | HDDC2 | CCDC152 | |
| MTIF | RSL24D1 | DRAM2 | CREM | ATP5E | FCRL3 | ATP6V0A1 | |
| CTSW | S100A6 | LEF1 | PRICKLE1 | DDX55 | EIF2S2 | SYTL1 | |
| CCL3 | S100A4 | HLA-F | ETFB | MAPKAPK2 | ACYP2 | SH3BGRL | |
| PIM1 | TAGLN | PABPC4 | C12orf75 | OXR1 | SATB1 | BLOC1S2 | |
| MT-ND4 | TRABD2A | TMIGD2 | RPS6 | SIGLEC10 | HMGB2 | CBR4 | |
| MGST2 | SYPL1 | LINC00402 | MIEN1 | RCSD1 | CCDC50 | ZNF385A | |
| CDC42 | CCDC28B | CSGALNACT1 | LY6E | AMICA1 | NIPAL3 | MED16 | |
| CST3 | NME4 | BATF | CD320 | C17orf89 | GIMAP7 | CD53 | |
| CD300A | CES1 | IL3RA | U2AF1L4 | TMSB4X | OAZ1 | CARD16 | |
| RTN3 | PROK2 | SLFN12 | LSP1_1 | DCXR | RPP38 | ADD1 | |
| TESPA1 | LEPROTL1 | TMEM204 | ORAI1 | NMRK1 | VCL | COX16 | |
| TCL1A | IPCEF1 | VAMP2 | MT-ND1 | THOC3 | METTL21A | DDX58 | |

TABLE 11-continued

The 1284 individually-varying genes.

| | | | | | | | |
|---|---|---|---|---|---|---|---|
| RPS5 | MRPL42 | VAMP5 | QPCT | IFIT1 | ADRBK2 | LILRA5 | |
| TRAPPC4 | ASAHI | BCL2A1 | SLC12A7 | PTPN18 | PLCL2 | PTGDS | |
| CD101 | CRISPLD2 | COX8A | SETBP1 | EHD1 | RAD51C | SEL1L3 | |
| TPGS2 | PTPLAD2 | MT-CO2 | ZFAND5 | TBXAS1 | COTL1 | RPL13 | |
| FCRL5 | CLECL1 | CXCL16 | SRD5A3 | MFN2 | BAZ2B | SUCLG1 | |
| CRIP2 | NDUFB2 | CD58 | PLCB1 | NDUFB8_1 | LIMA1 | CD180 | |
| PEX6 | BCAT1 | POP7 | CCSER2 | UBE2D1 | CCDC107 | CATSPER1 | |
| S100B | OASL | MTERFD2 | ITGA4 | CD7 | GBP1 | MAPKAPK3 | |
| PPDPF | ZFAS1 | KLF2 | LAP3 | CKLF | AHNAK | PGAM1 | |
| CD2 | ATP6V1D | CLIC3 | MCTP2 | INSIG1 | GGPS1 | SMAP2 | |
| ITGB2 | NDFIP1 | RP11-1143G9.4 | NMI | RP11-222K16.2 | RNF166 | RAMP1 | |
| EPHX2 | IL10RB | LRRC47 | KNSTRN | SPON2 | COG5 | MKNK1 | |
| LYPD2 | EPSTI1 | LDLRAP1 | CDC40 | APMAP | RP11-83A24.2 | DDX42 | |
| NUDT2 | CPNE2 | CD8A | HIATL1 | TP53I11 | POU2F2 | STOM | |
| C1orf162 | ODC1 | RPS16 | HERPUD1 | MRPL45 | PCNT | CERK | |
| NAIP | XBP1 | PLEK | DUSP22 | LY96 | PLEKHF1 | VCP | |
| NDUFA12 | EPHB6 | GIMAP6 | ANKRD28 | CCDC14 | PLBD1 | MAP3K13 | |
| FCGR2B | GCA | SSH2 | 44441 | CYP1B1 | UFL1 | AC004951.6 | |
| C10orf128 | PLCG2 | RPS18 | PTPRCAP | TOB1 | AIF1 | UPF1 | |
| RPL14 | DNAJC1 | RNASEH2C | 44257 | TAF7 | ZNF516 | TLR8 | |
| CYB5A | MYO1G | PPP1R2 | ARHGAP15 | ZNF302 | LNPEP | PRDX3 | |
| CMC1 | C6orf48 | TMEM258 | STARD3NL | MIB2 | BHLHE40 | CD36 | |
| KLRD1 | CMTM6 | RP11-362F19.1 | DHRS4L2 | SPOCK2 | DNAJB6 | WWC3 | |
| FAM101B | CISD3 | MGME1 | PHPT1 | MGST3 | AIM2 | GTF3C6 | |
| LYST | PPP2R2B | TAPBPL | C9orf78 | INADL | ECE1 | SRSF10_1 | |
| TESC | ITGB2-AS1 | WAC-AS1 | B2M | C10orf32 | SRGN | SEC24B | |
| FGFBP2 | PTGER4 | ANXA2 | AKIRIN1 | PAICS | NUCB2 | FUOM | |
| ZNF107 | PADI2 | PTPN4 | HSD17B10 | CTDSP1 | TSPAN3 | ARL11 | |
| ERAP2 | LPAR6 | GM2A | MAL | RXRA | CXorf21 | MTDH | |
| ITGB1 | PITPNA | MT-ND6 | IMMT | STAT1 | SETX | RASSF1 | |
| DZIP3 | SNHG7 | CDC42EP3 | SLC11A1 | CTSC | MTHFD1 | WDR41 | |
| STMN3 | REEP5 | ZFP36L2 | LGALS9 | NCK1 | PILRB | TMEM120B | |
| C12orf43 | MRPL44 | APOBEC3G | ID3 | CSTA | FBL | SLC36A4 | |
| CD27 | RAB27A | TXN | SLA | B4GALT3 | HERC5 | RYBP | |
| ZNF207 | PDIA6 | CARHSP1 | IER3 | IP6K2 | EPS8 | KDM5A | |
| IFI44L | MAP3K8 | SNN | TM2D3 | ARHGEF11 | GRAP2 | TNRC6A | |
| TNFSF10 | ARPC3 | VPS35 | ANXA1 | RHOC | FLT3LG | IDH2 | |
| FHIT | TUBA1B | RPL22L1 | LINC00909 | CLN5 | MMP24-AS1 | IRF2 | |
| IFNGR2 | SEC62 | ITGB7 | CKB | RAB28 | FAM96B | GALNT2 | |
| YBEY | RNASE6 | SH2D1B | GAPDH | RP11-664D1.1 | MORC3 | HEATR5B | |
| SLC35D2 | LYAR | UBE2L3 | NOP56 | KLRC4 | MALAT1 | TPST2 | |
| TMEM71 | FGL2 | BNIP3L | UBE2E2 | FES | JOSD1 | AC013264.2 | |
| IFIT3 | TMEM243 | TBCD | TMEM176B | KLF3 | TMEM63A | PRDX4 | |
| RNF149 | NKG7 | KDM6A | SASH1 | SOCS1 | SCIMP | SMARCA5 | |
| GS1-251I9.4 | C9orf142 | C12orf23 | TAGLN2 | SFSWAP | MANEA | PITPNA-AS1 | |
| BTLA | NOSIP | SSR4 | SESTD1 | CST7 | LACTB | LINC00116 | |
| MTSS1 | FGR | GSPT2 | C2CD5 | SURF1 | CD300LF | VPS26B | |
| CD226 | HOXB2 | YIF1A | VMA21 | NBPF1 | OXNAD1 | NUBP2 | |
| TSTD1 | SERF2 | CARD8 | UTRN | KHDRBS1 | PLEKHA5 | CCR1 | |
| MT1X | AP2S1 | MYO15B | CYBA | HAPLN3 | TSPAN32 | MAGT1 | |
| PRSS23 | POLR2J3 | LAIR1 | NDUFA6 | LINC00662 | EMR2 | FTL | |
| CNTNAP2 | PTMS | TADA3 | ZNF83 | TBX21 | BTG2 | AUP1 | |
| HLA-DQA1 | LTB4R | CUL1 | NKTR | ACSL1 | PRNP | RNF216 | |
| KDELR2 | PRKX | LYRM7 | DISC1 | PDCD6IP | DENND3 | RNASET2 | |
| CCDC88A | CLIC4 | CCR7 | BTN3A2 | SIK1 | MAP4K4 | WIPI2 | |
| FCRL6 | ADH5 | CEP85L | GPATCH11 | F8A1 | RBMX | RPS28 | |
| CD96 | MYLIP | POMC | TSPYL2 | TMEM156 | TMEM144 | THEMIS | |
| ITGB3BP | MGMT | ACTN1 | AC159540.1 | RPL36 | RARRES3 | CTSL | |
| DDX3X | OSCAR | FAM26F | LYRM4 | ABTB1 | PDE3B | | |
| FCER2 | TYMP | CALM1 | PRDX1 | ZC3H8 | FAS | | |
| CTSH | SIGIRR | ABLIM1 | MEAF6 | PTPN2 | LZIC | | |
| IFITM3 | GZMM | PRF1 | TNFRSF13B | BOLA3 | FAM63B | | |

TABLE 12

Top 250 individual genes for pathway analysis.

| | | | | | | | |
|---|---|---|---|---|---|---|---|
| RPS4Y1 | VSTM1 | ARHGAP24 | LINC00667 | KLRD1 | DDX3X | PDE4D | |
| HLA-DRB1 | PPA1 | BEX2 | EPB41L3 | FAM101B | FCER2 | CD3G | |
| RETN | CHPT1 | AC079767.4 | MT1F | LYST | CTSH | APEX1 | |
| SCGB3A1 | CD52 | IL32 | CTSW | TESC | IFITM3 | TRAT1 | |
| EIF1AY | CBWD2 | GTPBP6 | CCL3 | FGFBP2 | EBPL | NOP10 | |
| DDX3Y | TTC39C | VIM | PIM1 | ZNF107 | THBS1 | LILRB1 | |
| MZT2A | CCDC167 | RPS7 | MT-ND4 | ERAP2 | RPS9 | RABAC1 | |
| RPS26 | SMDT1 | ZRSR2 | MGST2 | ITGB1 | CROCCP2 | LGALS9B | |

TABLE 12-continued

Top 250 individual genes for pathway analysis.

| | | | | | | |
|---|---|---|---|---|---|---|
| XIST | RPL36AL | HLA-A | CDC42 | DZIP3 | CAPN12 | CEP78 |
| HLA-DQA2 | RIC3 | SERPINB6 | CST3 | STMN3 | SMARCA2 | KCNAB2 |
| MYOM2 | CCL5 | EIF2S3 | CD300A | C12orf43 | MARCO | NPDC1 |
| RP11-81H14.2 | MT2A | LINC00649 | RTN3 | CD27 | DAZAP2 | MX1 |
| GNLY | EIF5A | HLA-B | TESPA1 | ZNF207 | SKAP2 | S1PR5 |
| KANSL1-AS1 | NAPRT1 | HLA-DQB1 | TCL1A | IFI44L | RCBTB2 | CBWD1 |
| LTA4H | MT-CYB | USP53 | RPS5 | TNFSF10 | ITM2A | NABP1 |
| PRMT2 | CLEC12A | RASAL3 | TRAPPC4 | FHIT | SULF2 | SH3BGRL3 |
| CCZ1B | NSG1 | CSTB | CD101 | IFNGR2 | NCF1 | FLNA |
| CHI3L2 | RPL27A | TMEM8A | TPGS2 | YBEY | CHURC1 | TNFSF14 |
| CD151 | LITAF | SULT1A1 | FCRL5 | SLC35D2 | GBP3 | PLXNC1 |
| LILRA3 | LAIR2 | LGALS1 | CRIP2 | TMEM71 | ATHL1 | ARPC1B |
| CHCHD2 | MXRA7 | C8orf59 | PEX6 | IFIT3 | NDUFS5 | DDT |
| EIF1AX | FRG1B | LDLR | S100B | RNF149 | SCN3A | SNAPC5 |
| TIMM10 | LIPA | AL592183.1 | PPDPF | GS1-251I9.4 | ATP6V1G1 | NPIPB5 |
| SIGLEC14 | BIN1 | NAAA | CD2 | BTLA | CENPK | GYPC |
| FCER1G | HLA-E | THEMIS2 | ITGB2 | MTSS1 | SYNGR1 | CCL4 |
| RPS4X | LYZ | KCNMA1 | EPHX2 | CD226 | BCL7C | IL7R |
| DIP2A | EMR1 | MT-ATP6 | LYPD2 | TSTD1 | YWHAQ | RRP7A |
| SNHG8 | HLA-DRA | PSMD5-AS1 | NUDT2 | MT1X | LTBP3 | CPNE1 |
| HLA-C | TNFSF13B | GIMAP4 | C1orf162 | PRSS23 | STXBP2 | IFI44 |
| AK5 | MYL12A | APOBEC3A | NAIP | CNTNAP2 | EIF4E3 | ID2 |
| FCGR3A | SUMF2 | PSTPIP2 | NDUFA12 | HLA-DQA1 | MERTK | KLRG1 |
| DAPK1 | PPT1 | CD3E | FCGR2B | KDELR2 | AP1S2 | IFI6 |
| CNN2 | ARL17A | HOPX | C10orf128 | CCDC88A | RPL28 | TMEM18 |
| RPS10 | CD300C | LGALS2 | RPL14 | FCRL6 | CD55 | XRRA1 |
| FOLR3 | FIBP | RPS13 | CYB5A | CD96 | CFD | |
| CCZ1 | GTF2H2 | GZMH | CMC1 | ITGB3BP | EBP | |

TABLE 13

Top 250 diurnal genes for pathway analysis.

| | | | | | | |
|---|---|---|---|---|---|---|
| DDIT4 | LSP1_1 | SAMD4B | PIEZO1 | CLDND1 | CEBPD | WIPF2 |
| TYROBP | STK10 | KLF4 | RAB18 | HDAC10 | AKAP13 | STIM2 |
| COX5B | CX3CR1 | PPIB | IL2RB | RPL28 | EEF1B2 | S100A9 |
| RPS9 | PCBP2 | MBD6 | ALCAM | SELPLG | DNPH1 | LINC01116 |
| NCR3 | VIM-AS1 | HBB | DENND4B | NEAT1 | CYSTM1 | HNRNPC |
| SNORA76 | CTDSP2 | RPL32 | AP2M1 | SPON2 | CTSA | LMO4 |
| RPS2 | GNAS | USP15 | ERGIC3 | SAP30 | CELF1 | UBALD2 |
| MT-ND3 | HIGD2A | RENBP | FLOT2 | NOL12 | TSPO | HCFC1 |
| PCBP1 | CORO7 | C16orf54 | SH2D3C | RPL18 | HIVEP2 | MXD4 |
| ABCA2 | NDUFB9 | CALR | GIMAP6 | TSC22D3 | DBP | SYTL3 |
| RPL19 | MT-ND2 | RPL39 | TFEB | MYL6 | EIF4B | TCEB3 |
| CBFA2T2 | RNFT1 | RSPH3 | HAPLN3 | TFAM | ARF6 | NDUFA3 |
| CDC42SE2 | CRIP1_1 | INPPL1 | MT-ND5 | TUBA1A | VPS28 | SESN1 |
| LMO2 | CD180 | CBX7 | AKNA | CALM1 | TMBIM6 | CHCHD10 |
| RPS8 | PDIA3 | CDIP1 | SEC16A | EIF3K | TBL1X | ZBTB16 |
| CELF2 | MAU2 | SGPP1 | CYTH4 | TCEB2 | MOB3A | FBXO32 |
| RPS15 | ISG20 | ITGB2 | MORF4L1 | FAU | LINC00324 | SRGAP2 |
| GPR65 | RPL36AL | PTBP1 | TRIP11 | C19orf24 | DAZAP2 | GABARAP |
| EIF4A2 | BTG1 | TGFBR2 | IRF4 | PRDM1 | PRMT1 | ZFP36 |
| SMAP2 | GZMM | ZC2HC1A | SSNA1 | STAG3 | GBP4 | HSP90AB1 |
| MAT2B | CXCR4 | TCF7 | S1PR1 | CXCR3 | DPH3 | ITGA4 |
| RSL1D1 | IGLL5 | TRAPPC6A | COX4I1 | HCST | CAT | MAN2B2 |
| RPL11 | IFI16 | TMC8 | MYD88 | FDX1 | SH3BP1 | TP53 |
| FPR1 | RPL35A | FLNA | ANKRD49 | MT-CO1 | CYB561 | CASP2 |
| LINC00649 | RPL6 | C9orf142 | GPATCH4 | CTSW | PAFAH1B2 | CRELD2 |
| RPL13 | TMEM106A | CYSLTR1 | OGDH | ATP5I | ZNF429 | BRI3 |
| SREK1IP1 | MT-ND4 | C19orf53 | PPM1K | AGPAT1 | YTHDC2 | C19orf10 |
| RBM3 | RC3H1 | SERF2 | TOR3A | KPNA6 | WDR60 | RRAGC |
| HSPA5 | SERPINB1 | HADHA | ZDHHC2 | ANXA5 | HOTAIRM1 | GNB2L1 |
| TXNIP | RPS18 | SUN2 | RPS24 | MIR142 | TLR7 | HELZ2 |
| RPS14 | FMNL1 | PPP2R1A | NCOA2 | TNRC6B | PANK3 | GZMH |
| SLC25A6 | SEC61B | CYTIP | POU2F2 | NFE2 | RAB1B | TRANK1 |
| RPL7A | MT-ND1 | PNRC1 | MAP2K1 | PLBD1 | ARHGAP17 | SLFN11 |
| LIMD1 | SF1 | TAF1D | SLA | RPL5 | LRRC8D | GAPDH |
| MPEG1 | FKBP5 | S100A6 | AHNAK | NKG7 | EZR | |
| CD55 | MRPL52 | RPS25 | ZCCHC17 | ST3GAL5 | ARPC1B | |

Altogether, these data demonstrated that small volume capillary blood samples can be used for gene profiling, including immune profiling.

ADDITIONAL CONSIDERATIONS

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Accordingly, phrases such as "a device configured to" are intended to include one or more recited devices. Such one or more recited devices can also be collectively configured to carry out the stated recitations. For example, "a processor configured to carry out recitations A, B and C can include a first processor configured to carry out recitation A and working in conjunction with a second processor configured to carry out recitations B and C. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

It will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence, can be added, merged, or left out altogether (for example, not all described acts or events are necessary for the practice of the algorithms). Moreover, in certain embodiments, acts or events can be performed concurrently, for example through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A method for single cell ribonucleic acid sequencing comprising:
providing a first capillary blood sample obtained from a subject at a first time point;
diluting the first sample to obtain a first diluted sample;
isolating first capillary peripheral blood mononuclear cells (cPBMCs) from the first diluted sample with gradient centrifugation;
performing single cell ribonucleic acid sequencing (scRNA-seq) on the first cPBMCs isolated to generate first scRNA-seq data; and
determining a first scRNA profile of the subject at the first time point using the first scRNA-seq data and single-nucleotide polymorphisms (SNPs) of the subject.

2. The method of claim 1, comprising:
providing a second capillary blood sample obtained from the subject at a second time point;
diluting the second sample to obtain a second diluted sample;
isolating second cPBMCs from the second diluted sample with gradient centrifugation;
performing scRNA-seq on the second cPBMCs isolated to generate second scRNA-seq data; and
determining a second scRNA profile of the subject at the second time point using the second scRNA-seq data and SNPs of the subject.

3. The method of claim 2, wherein the first time point and the second time point are about 2 hours to about 24 hours apart.

4. The method of claim 2, wherein the subject is in a first health state at the first time point, and wherein the subject is in a second health state at the second time point.

5. The method of claim 4,
wherein the first health state at the first time point comprises a first disease state of a disease and the second health state at the second time point comprises a second disease state of the disease,
wherein the first health state at the first time point comprises first symptoms and the second health state at the second time point comprises second symptoms,
wherein the first symptoms and the second symptoms are identical, the first symptoms and the second symptoms are different, the first symptoms comprise the second symptoms, and/or the second symptoms comprise the first symptoms, and/or
wherein the first symptoms and the second symptoms comprise an identical symptom of different severities.

6. The method of claim 4, comprising:
correlating the first health state of the subject at the first time point with the first scRNA profile of the subject at the first time point; and/or
correlating the second health state of the subject at the second time point with the second scRNA profile of the subject at the second time point.

7. The method of claim 4, comprising:
determining a difference between the scRNA profile of the subject at the first time point and the second scRNA profile of the subject at the second time point, optionally thereby determining one or more genes of interest, optionally wherein the one or more genes of interest comprise diurnal genes and/or one or more genes each with a time of day variation in the first scRNA profile and the second scRNA profile;

designing a gene panel comprising the one or more genes of interest; and/or determining a difference between the first health state of the subject at the first time point and the second health state of the subject at the second time point.

8. The method of claim 7, comprising:

correlating (i) the difference between the scRNA profile of the subject at the first time point and the second scRNA profile of the subject at the second time point and (ii) the difference between the first health state of the subject at the first time point and the second health state of the subject at the second time point.

9. The method of claim 2, wherein said determining comprises: performing sample demultiplexing of the first scRNA data of the subject and/or the second scRNA data of the subject using SNPs of the subject to determine the first scRNA profile of the subject and/or the second scRNA profile of the subject.

10. The method of claim 1, wherein the scRNA-seq comprises a whole transcriptome scRNA-seq, and wherein the scRNA profile comprises a whole transcriptome profile.

11. The method of claim 1, wherein the first sample has a volume of about 20 µl to about 500 µl.

12. The method of claim 1, wherein the first sample is collected by the first subject.

13. The method of claim 1, wherein the first sample is collected in a non-clinical setting and/or out of clinic.

14. The method of claim 1, wherein the first sample is collected using a device comprising microneedles, a device comprising microfluidic channels, a push-button collection device, or a combination thereof.

15. The method of claim 1, wherein said diluting comprises a 1:2 to 1:50 dilution.

16. The method of claim 1, wherein the scRNA-seq comprises a target scRNA-seq, and wherein the scRNA profile comprises expression information of a plurality of at most 1,000 genes.

17. The method of claim 2, wherein the first sample and/or the second sample is collected from a deltoid or a finger of the subject at the first time point and/or a deltoid or a finger of the subject at the second time point.

18. The method of claim 2, wherein said diluting comprises diluting the first sample and/or the second sample having a volume of about 100 µl to about 1 ml.

19. The method of claim 1, wherein said isolating comprises isolating the first cPBMCs with gradient centrifugation using a density medium with a density of about 1 g/ml to about 1.5 g/ml, wherein a duration of the density centrifugation is about 10 mins to about 30 mins, and/or wherein a speed of the density centrifugation is about 500 RPM to about 1500 RPM.

20. The method of claim 2, wherein the second sample has a volume of about 20 µl to about 500 µl.

* * * * *